United States Patent
Borden et al.

(10) Patent No.: US 10,058,837 B2
(45) Date of Patent: Aug. 28, 2018

(54) SYSTEMS, METHODS, AND DEVICES FOR PRODUCTION OF GAS-FILLED MICROBUBBLES

(75) Inventors: Mark A. Borden, Boulder, CO (US); Edward J. Swanson, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 1301 days.

(21) Appl. No.: 13/392,520

(22) PCT Filed: Aug. 26, 2010

(86) PCT No.: PCT/US2010/046854
§ 371 (c)(1),
(2), (4) Date: Mar. 30, 2012

(87) PCT Pub. No.: WO2011/025893
PCT Pub. Date: Mar. 3, 2011

(65) Prior Publication Data
US 2012/0175305 A1    Jul. 12, 2012

Related U.S. Application Data

(60) Provisional application No. 61/237,892, filed on Aug. 28, 2009, provisional application No. 61/371,332, filed on Aug. 6, 2010.

(51) Int. Cl.
*B01F 11/02* (2006.01)
*B01J 13/04* (2006.01)
*A61K 49/22* (2006.01)

(52) U.S. Cl.
CPC .............. *B01J 13/04* (2013.01); *A61K 49/223* (2013.01)

(58) Field of Classification Search
None
See application file for complete search history.

(56) References Cited

U.S. PATENT DOCUMENTS 3,598,111 A    8/1971  Kahn et al.
4,070,167 A *  1/1978  Barbee ............... B01D 19/0078
                                                      118/602

(Continued)

FOREIGN PATENT DOCUMENTS

WO    1997000638 A2    1/1997
WO    1998018501 A2    5/1998

(Continued)

OTHER PUBLICATIONS

Chang et al., "3-D US Frame Positioning Using Speckle Decorrelation and Image Registration," *Ultrasound in Medicine & Biology*, Jun. 2003, 29(6): pp. 801-812.

(Continued)

*Primary Examiner* — Bobby Ramdhanie
*Assistant Examiner* — Michael J An
(74) *Attorney, Agent, or Firm* — Potomac Law Group, PLLC; Mark Catan

(57) ABSTRACT

Gas-filled microbubbles can be synthesized using a continuous flow chamber and a sonicator. The resulting microbubble solution can be size-sorted for a particular application, such as injection into a patient for gas delivery thereto. The microbubble solution may be concentrated to have greater than 50% volume gas while maintaining microbubble sizes below 10 μm. Control of the microbubble generation process can yield highly stable microbubbles. The microbubbles may retain over half of their original gas payload for over three weeks while exhibiting minimal change in microbubble size. The systems, methods, and devices described herein thus allow for continuous or batchwise continuous production of gas-filled microbubbles that (Continued)

readily release their gas payload when introduced into an under-saturated or de-saturated solution.

7 Claims, 10 Drawing Sheets

(56) References Cited

U.S. PATENT DOCUMENTS

| | | | |
|---|---|---|---|
| 4,421,503 A * | 12/1983 | Latham et al. | 494/17 |
| 4,440,921 A | 4/1984 | Allcock et al. | |
| 4,495,174 A | 1/1985 | Allcock et al. | |
| 4,757,128 A | 7/1988 | Domb et al. | |
| 4,777,599 A | 10/1988 | Dorogi et al. | |
| 4,789,724 A | 12/1988 | Domb et al. | |
| 4,842,738 A | 6/1989 | Greenspan | |
| 4,857,311 A | 8/1989 | Domb et al. | |
| 4,880,622 A | 11/1989 | Allcock et al. | |
| 4,888,176 A | 12/1989 | Langer et al. | |
| 4,946,938 A | 8/1990 | Magill et al. | |
| 4,957,656 A | 9/1990 | Cerny et al. | |
| 4,971,731 A | 11/1990 | Zipperian | |
| 5,107,837 A | 4/1992 | Ophir et al. | |
| 5,123,414 A | 6/1992 | Unger | |
| 5,178,147 A | 1/1993 | Ophir et al. | |
| 5,309,914 A | 5/1994 | Iinuma | |
| 5,380,519 A | 1/1995 | Schneider et al. | |
| 5,435,310 A | 7/1995 | Sheehan et al. | |
| 5,531,980 A | 7/1996 | Schneider et al. | |
| 5,567,414 A | 10/1996 | Schneider et al. | |
| 5,601,084 A | 2/1997 | Sheehan et al. | |
| 5,605,673 A * | 2/1997 | Schutt et al. | 424/9.51 |
| 5,606,971 A | 3/1997 | Sarvazyan | |
| 5,643,553 A | 7/1997 | Schneider et al. | |
| 5,658,551 A | 8/1997 | Schneider et al. | |
| 5,662,113 A | 9/1997 | Liu | |
| 5,665,383 A | 9/1997 | Grinstaff et al. | |
| 5,722,411 A | 3/1998 | Suzuki et al. | |
| 5,741,522 A | 4/1998 | Violante et al. | |
| 5,810,731 A | 9/1998 | Sarvazyan et al. | |
| 5,840,028 A | 11/1998 | Chubachi et al. | |
| 5,855,865 A | 1/1999 | Lambert et al. | |
| 5,874,500 A | 2/1999 | Rhee et al. | |
| 5,911,972 A | 6/1999 | Schneider et al. | |
| 5,928,151 A | 7/1999 | Hossack et al. | |
| 6,028,066 A | 2/2000 | Unger | |
| 6,102,864 A | 8/2000 | Hatfield et al. | |
| 6,102,865 A | 8/2000 | Hossack et al. | |
| 6,110,443 A | 8/2000 | Schneider et al. | |
| 6,123,669 A | 9/2000 | Kanda | |
| 6,136,293 A | 10/2000 | Schneider et al. | |
| 6,193,951 B1 | 2/2001 | Ottoboni et al. | |
| 6,210,611 B1 | 4/2001 | Needham et al. | |
| 6,217,850 B1 | 4/2001 | Dugstad et al. | |
| 6,241,675 B1 | 6/2001 | Smith et al. | |
| 6,245,318 B1 | 6/2001 | Klibanov et al. | |
| 6,246,895 B1 | 6/2001 | Plewes | |
| 6,312,382 B1 | 11/2001 | Mucci et al. | |
| 6,352,507 B1 | 3/2002 | Torp et al. | |
| 6,508,768 B1 | 1/2003 | Hall et al. | |
| 6,537,217 B1 | 3/2003 | Bjærum et al. | |
| 6,537,221 B2 | 3/2003 | Criton et al. | |
| 6,649,145 B2 | 11/2003 | McGrath et al. | |
| 6,671,541 B2 | 12/2003 | Bishop et al. | |
| 6,683,454 B2 | 1/2004 | Rehwald et al. | |
| 6,685,641 B2 | 2/2004 | Liu | |
| 6,703,047 B2 | 3/2004 | Sawhney et al. | |
| 6,770,051 B2 | 8/2004 | Hughes et al. | |
| 6,875,176 B2 | 4/2005 | Mourad et al. | |
| 6,896,659 B2 | 5/2005 | Conston et al. | |
| 6,930,087 B2 | 8/2005 | Baru et al. | |
| 7,055,378 B2 | 6/2006 | Su et al. | |
| 7,083,572 B2 | 8/2006 | Unger et al. | |
| 7,109,167 B2 | 9/2006 | Wronski et al. | |
| 7,115,583 B2 | 10/2006 | Porter et al. | |
| 7,257,244 B2 | 8/2007 | Miga | |
| 7,331,926 B2 | 2/2008 | Varghese et al. | |
| 7,421,101 B2 | 9/2008 | Georgescu et al. | |
| 7,601,122 B2 | 10/2009 | Zagzebski et al. | |
| 7,753,847 B2 | 7/2010 | Greenleaf et al. | |
| 8,029,444 B2 | 10/2011 | Pedrizzetti et al. | |
| 8,167,280 B2 * | 5/2012 | Chomas | B01F 5/0682 239/8 |
| 2002/0034757 A1 | 3/2002 | Cubicciotti | |
| 2002/0039594 A1 | 4/2002 | Unger | |
| 2002/0065461 A1 | 5/2002 | Cosman | |
| 2002/0102217 A1 | 8/2002 | Klaveness et al. | |
| 2002/0192632 A1 | 12/2002 | Hei et al. | |
| 2003/0078227 A1 | 4/2003 | Greenleaf et al. | |
| 2003/0220556 A1 | 11/2003 | Porat et al. | |
| 2004/0006266 A1 | 1/2004 | Ustuner et al. | |
| 2004/0059224 A1 | 3/2004 | Varghese et al. | |
| 2004/0092816 A1 | 5/2004 | Ossmann et al. | |
| 2004/0180004 A1 | 9/2004 | Schneider et al. | |
| 2004/0249580 A1 | 12/2004 | Pourcelot et al. | |
| 2004/0253183 A1 | 12/2004 | Uber et al. | |
| 2005/0004466 A1 | 1/2005 | Hynynen et al. | |
| 2005/0054930 A1 | 3/2005 | Rickets et al. | |
| 2005/0059876 A1 | 3/2005 | Krishnan et al. | |
| 2005/0080336 A1 | 4/2005 | Byrd et al. | |
| 2005/0084538 A1 | 4/2005 | Dayton et al. | |
| 2005/0175541 A1 | 8/2005 | Lanza et al. | |
| 2005/0201942 A1 | 9/2005 | Dugstad et al. | |
| 2005/0260189 A1 | 11/2005 | Klibanov et al. | |
| 2005/0267695 A1 | 12/2005 | German | |
| 2005/0271560 A1 * | 12/2005 | Rodgers et al. | 422/130 |
| 2006/0002994 A1 | 1/2006 | Thomas et al. | |
| 2006/0034904 A1 | 2/2006 | Weimann | |
| 2006/0058673 A1 | 3/2006 | Aase et al. | |
| 2006/0074315 A1 | 4/2006 | Liang et al. | |
| 2006/0173320 A1 | 8/2006 | Radulescu | |
| 2007/0020224 A1 | 1/2007 | Vetter et al. | |
| 2007/0049824 A1 | 3/2007 | Konofagou et al. | |
| 2007/0060906 A1 | 3/2007 | Wu | |
| 2007/0071685 A1 | 3/2007 | Schneider et al. | |
| 2007/0081946 A1 | 4/2007 | Schneider et al. | |
| 2007/0128117 A1 | 6/2007 | Bettinger et al. | |
| 2007/0203166 A1 | 8/2007 | Shorr et al. | |
| 2007/0207194 A1 | 9/2007 | Grayburn et al. | |
| 2007/0219447 A1 | 9/2007 | Kanai et al. | |
| 2007/0276242 A1 | 11/2007 | Konofagou | |
| 2007/0276245 A1 | 11/2007 | Konofagou | |
| 2008/0008657 A1 | 1/2008 | Bussat et al. | |
| 2008/0145311 A1 | 6/2008 | Lanza et al. | |
| 2008/0194957 A1 | 8/2008 | Hoctor et al. | |
| 2008/0200417 A1 | 8/2008 | Semple et al. | |
| 2008/0206131 A1 | 8/2008 | Jaffray et al. | |
| 2008/0260802 A1 | 10/2008 | Sawhney et al. | |
| 2008/0269606 A1 | 10/2008 | Matsumura | |
| 2008/0269668 A1 | 10/2008 | Keenan et al. | |
| 2008/0285819 A1 | 11/2008 | Konofagou et al. | |
| 2008/0311045 A1 | 12/2008 | Hardy | |
| 2008/0319375 A1 | 12/2008 | Hardy | |
| 2009/0011004 A1 | 1/2009 | Lutz et al. | |
| 2009/0123435 A1 | 5/2009 | Ratcliffe et al. | |
| 2009/0191244 A1 | 7/2009 | Kheir et al. | |
| 2009/0192439 A1 | 7/2009 | Lamson et al. | |
| 2010/0003195 A1 | 1/2010 | Sato et al. | |
| 2011/0208038 A1 | 8/2011 | Konofagou et al. | |

FOREIGN PATENT DOCUMENTS

| | | |
|---|---|---|
| WO | 1999053963 A1 | 10/1999 |
| WO | 2000044808 A1 | 8/2000 |
| WO | 2001008711 A2 | 2/2001 |
| WO | 2008015012 A1 | 2/2008 |
| WO | 2008131217 A1 | 10/2008 |
| WO | WO 2009/043031 | 4/2009 |
| WO | WO 2010/044385 | 4/2010 |
| WO | WO 2010/063951 | 6/2010 |
| WO | 2011025893 A1 | 3/2011 |
| WO | 2011028690 A1 | 3/2011 |
| WO | 2011034892 A2 | 3/2011 |
| WO | 2011075557 A1 | 6/2011 |
| WO | 2011139927 A1 | 11/2011 |

(56) References Cited

FOREIGN PATENT DOCUMENTS

| WO | 2012019146 A1 | 2/2012 |
|---|---|---|
| WO | 2012019172 A1 | 2/2012 |
| WO | 2012030675 A1 | 3/2012 |

OTHER PUBLICATIONS

Avolio et al., "Effects of aging on changing arterial compliance and left ventricular load in a northern Chinese urban community," Circulation, vol. 68(1), pp. 50-58, 1983.
Badke et al., (1980) "Effects of ventricular pacing on regional left ventricular performance in the dog," Am J Physiol Heart Circ Physiol 238:H858-867.
Bercoff et al., "Supersonic Shear Imaging: A new technique for soft tissue elasticity mapping," IEEE Transactions on Ultrasonics, Ferroelectrics, and Frequency Control, vol. 51(4), pp. 396-409, Apr. 2004.
Berger et al., (2006) "Single-Beat Noninvasive Imaging of Cardiac Electrophysiology of Ventricular Pre-Excitation. Journal of the American College of Cardiology," 48(10):2045-2052.
Bers, D.M., "Cardiac excitation-contraction coupling", Nature, Jan. 10, 2002, vol. 415:198-205.
Bonnefous et al., "Time domain formulation of pulse-Doppler ultrasound and blood velocity estimation by cross-correlation," Ultrason Imaging, vol. 8(2), pp. 73-85, Apr. 1986.
Borden et al., "Ultrasound Radiation Force Modulates Ligand Availability on Target Contrast Agents," Mol. Imaging, 5:139-147 (2006).
Brooks et al., "Electrical Imaging of the Heart," IEEE Signal Processing Magazine, vol. 14(1), pp. 24-42, Jan. 1997.
Campbell et al., "Mechanisms of transmurally varying myocyte electromechanics in an integrated computational model," Phl. Trans. R. Soc. A., 366:3361-3380, Jul. 1, 2008.
Chen et al., "Radiation-force-based estimation of acoustic attenuation using harmonic motion imaging," Sep. 2012, p. 1983 in "Biomedical Acoustics and Signal Processing in Acoustics: Measurement of Material Properties Using Wave Propagation Methods," *Journal of the Acoustical Society of America*, Sep. 2012, 3(2): pp. 1980-2018.
Cobbold, R.S.C., "Foundations of biomedical ultrasound," 2007, Biomedical engineering series, Oxford University Press, pp. 422-423.
Cutnell et al., Table of Contents for "Physics," Fourth Edition, 1998, New York.
Damianou et al., "Dependence of Ultrasonic Attenuation and absorption in dog soft tissues on Temperature and Thermal dose," The Journal of Acoustical Society of America, 102(1):628-634 (1997).
De Craene et al., "Temporal diffeomorphic free-form deformation: Application to motion and strain estimation from 3D echocardiography," Medical Image Analysis, 16(2):427-450 (2012).
Declerck et al., "Left ventricular motion reconstruction from planar tagged MR images: a comparison," Phys Med Biol, vol. 45(6), pp. 1611-1632, Jun. 2000.
DuBose et al., "Confusion and Direction in Diagnostic Doppler Sonography," Journal of Diagnostic Medical Sonography, 25(3):173-177 (2009).
Duck, F.A., Table of Contents for "Physical Properties of Tissue: A Comprehensive Reference Book," 1990, Academic Press Ltd., London, UK.
Duerinckx et al., "In vivo Acoustic Attentuation in Liver: Correlations with Blood Tests and Histology," Ultrasonic in Medicine & Biology, 14(5):405-413 (1988).
Durrer et al. (1970) "Total Excitation of the Isolated Human Heart." Circulation, 41:899-912.
Edwards et al., "Effects of Ischemia on Left-Ventricular Regional Function in the Conscious Dog," American Journal of Physiology, vol. 240, pp. H413-H420, 1981.

Extended European Search Report, dated May 6, 2014, for European Application No. 10838238.3.
Faris et al. (2003) "Novel Technique for Cardiac Electromechanical Mapping with Magnetic Resonance Imaging Tagging and an Epicardial Electrode Sock," Ann Biomed Eng. 31:430-440.
Fenster et al., "Three-dimensional ultrasound imaging," Physics in Medicine and Biology, 46(5):R67-R99 (2001).
Fujii et al., "A New Method for Attenuation Coefficient Measurement in the Liver," Journal of Ultrasound in Medicine, 21(7):783-788 (2002).
Fung, Y.C., Table of Contents for "Biomechanics—Mechanical Properties of Living Tissues," 1993, Springer-Verlag, New York.
Ginat et al., "High-resolution ultrasound elastography of articular cartilage in vitro," *Proceedings of the 28th IEEE EMBS Annual International Conference, New York City, USA* pp. 6644-6647 (Aug. 30-Sep. 3, 2006).
Greenstein et al., (2006) "Mechanisms of Excitation-Contraction Coupling in an Integrative Model of the Cardiac Ventricular Myocyte," Biophysical Journal 90:77-91.
Greenwald, S.E., "Pulse pressure and arterial elasticity," QJM: An International Journal of Medicine, vol. 95(2), pp. 107-112, 2002.
Gupta et al., "Changes in Passive mechanical Stiffness of Myocardial Tissue with Aneurysm Formation," Circulation, vol. 89, pp. 2315-2326, 1994.
Gurev et al., "Distribution of Electromechanical Delay in the Heart: Insights from a Three-Dimensional Electromechanical Model," Biophysical Journal 99:745-754, Aug. 2010.
Gurev et al., "In silico characterization of ventricular activation pattern by electromechanical wave imaging," Poster Session 5, PO05-80, Supplement to Heart Rhythm 6: p. S357.
Heimdal et al., "Real-time strain rate imaging of the left ventricle by ultrasound," J Am Soc Echocardiog, vol. 11(11), pp. 1013-1019, 1998.
Henderson et al., "Series Elasticity of Heart Muscle During Hypoxia," Cardiovascular Research, vol. 5, pp. 10-14, 1971.
Housden et al., "Ultrasonic imaging of 3D displacement vectors using a simulated 2D arrary and beamsteering," Ultrasonics, 53(2):615-621 (2013).
Huang et al., "Watershed Segmentation for Breast Tumor in 2-D Sonography," May 2004, Ultrasound in Medicine and Biology, pp. 625-632.
International Search Report for International Application No. PCT/US11/34704, dated Aug. 18, 2011.
Jasaityte et al., "Current state of three dimensional myocardial strain estimation using echocardiography," Journal of the American Society of Echocardiography, 26(1):15-28 (2013).
Jensen et al., "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.
Kallel et al., "A least-squares strain estimator for elastography," Ultrasonic Imaging, 1997, 19:195-208.
Kanai et al., "A New Method for Measuring Small Local Vibrations in the Heart Using Ultrasound," IEEE T Bio-Med Eng, vol. 40(12), pp. 1233-1242, Dec. 1993.
Kanai et al., "Myocardial rapid velocity distribution," Ultrasound Med. & Biol., vol. 27(4), pp. 481-498, Apr. 2001.
Kanai et al., "Transcutaneous measurement of frequency dispersion in the regional pulse wave velocity," IEEE Ultrasonics Symposium, 2000.
Kanai, H., "Propagations of spontaneously actuated pulsive vibration in human heart wall and in vivo viscoelasticity estimation," IEE Transaction on Ultrasonics, Ferroelectrics, and Frequency Control, vol. 52(11), pp. 1931-1942, Nov. 2005.
Kimber et al. (1996) "A Comparison of Unipolar and Bipolar Electrodes During Cardiac Mapping Studies," Pacing Clin Electro 19:1196-1204.
Konofagou et al., "A New Elastographic Method for Estimation and Imaging od Lateral Strains, Corrected Axial Strains and Poisson's Ratios in Tissues," Ultrasound in Medicine & Biology 24(8): 1183-1199, 1998.

(56) References Cited

OTHER PUBLICATIONS

Konofagou et al., "Electromechanical Wave imaging for noninvasive mapping of the 3D electrical activation sequence in canines and humans in vivo,"Journal of Biomechanics, 45(5):856-864 (Mar. 15, 2012).
Konofagou et al., "Myocardial Elastography—Feasibility Study in Vivo," Ultrasound Med & Biol, vol. 28(4), pp. 475-482, Apr. 2002.
Konofagou et al., "Noninvasive Electromechanical Wave Imaging and Conduction Velocity Estimation In Vivo," Ultrasonics Symposium, 2007 IEEE, pp. 969-972, 2007.
Konofagou et al., "Noninvasive electromechanical wave imaging and conduction-relevant velocity estimation in vivo," Ultrasonics,50(2):208-215 (2010).
Konofagou et al., "Three-dimensional Motion estimation in Elastography," IEEE Proceedings of the Symposium of Ultrasonics, Ferroelectrics, and Frequency Control in Sendai Japan, pp. 1745-1748, vol. 2, 1998.
Konofagou et al., "Elastographic Imaging of the Strain Distribution at the Anterior Cruciate Ligament and ACL-Bone Insertions" 27th Annual International Conference of the Engineering in Medicine and Biology Society, pp. 972-975 (Shanghai, China Sep. 1-4, 2005).
Lai et al., Table of Contents for "Introduction to Continuum Mechanics," Third Edition, 1993, Pergamon Press, New York.
Lee et al., "Theoretical Quality Assessment of Myocardial Elastography with In Vivo Validation," Ultrasonics, Ferroelectrics and Frequency Control, IEEE Transactions on 54(1):2233-2245, Nov. 11, 2007.
Luo et al., "A fast normalized cross-correlation method for motion estimation," IEEE Trans. Ultrason. Ferroelectr. Control 57(6): 1347-1357, Jun. 2010.
Luo et al., "High-frame rate, full-view myocardial elastography with automated contour tracking in murine left ventricles in vivo," IEEE Transactions on Ultrasonics, Ferroelectrics and Frequency Control, 55(1):240-248, Jan. 2008.
Luo et al., "Myocardial elastography at both high temporal and spatial resolution for the detection of infarcts," Ultrasound in Med. & Bio, vol. 33(8), pp. 1206-1223, Aug. 2007.
Luo et al., "Pulse wave imaging of normal and aneurysmal abdominal aortas in vivo", IEEE Trans. Med. Imaging 28(4): 477-486, 2009.
Maleke et al., "In Vivo Feasibility of Real-time Monitoring of Focused Ultrasound Surgery (FUS) Using Harmonic Motion Imaging (HMI)," IEEE Trans. Biomed. Eng., vol. 57(1), pp. 7-11, Jan. 2010.
Maleke et al., "Single-Element focused Ultrasound Transducer Method for Harmonic Motion Imaging," Ultrason. Imagin, vol. 28, No. 3, pp. 144-158, 2006.
McLaughlin et al., "Piezoelectric sensor determination of arterial pulse wave velocity," Physiol. Meas., vol. 24(3), pp. 693-702, 2003.
Mitri et al., "Chirp imaging vibro-acoustography for removing the ultrasound standing wave artifact," IEEE transactions on medical imaging, vol. 24(10), pp. 1249-1255, Oct. 2005.
Nichols et al., Table of Contents for "McDonald's blood flow in arteries: theoretic, experimental, and clinical principles," 4th Edition, 1998, Oxford University Press, New York.
Ophir et al., "Elastography: A quantitative method for imaging the elasticity of biological tissues," Ultrasonic Imaging, vol. 13(2), pp. 111-134, 1991.
Otani et al., "Transmural ultrasound-based visualization of patterns of action potential wave propagation in cardiac tissue," Annals Biomedical Engineering, 38(10):3112-3123 (2010).
Otani et al., "Use of ultrasound imaging to map propagating action potential waves in the heart," Computers in Cardiology, 36:617-620 (2009).
Palmeri et al., "Characterizing Acoustic Attenuation of Homogeneous Media Using Focused Impulsive Acoustic Radiation Force," Ultrasonic Imaging, 28(2):114-128 (2006.
Papadakis, E.P., Table of Contents for "Ultrasonic Instruments & Devices: Reference for Modern Instrumentation, Techniques, and Technology," 1999, Academic Press, New York.
Pernot et al., "Electromechanical Imaging of the Myocardium at Normal and Pathological States", Ultrasonics Symposium, 2005 IEEE, pp. 1091-1094, 2005.
Pernot et al.,(2007) "ECG-gated, Mechanical and Electromechanical Wave Imaging of Cardiovascular Tissues In Vivo," Ultrasound in Medicine & Biology 33(7):1075-1085.
Prinzen et al., (1992) "The time sequence of electrical and mechanical activation during spontaneous beating and ectopic stimulation," Eur Heart J 13:535-543.
Provost et al., "In Vivo Validation of 2D Myocardial Elastography at Variable Levels of Ischemia," 2008 IEEE International Ultrasonics Symposium Proceedings, pp. 962-965.
Provost et al., "Imaging the electromechanical activity of the heart in vivo," Proceedings of the National Academy of Sciences, 108:8565-8570 (2011).
Provost et al., "Mapping of cardiac electrical activation with electromechanical wave imaging: An in silico-in vivo reciprocity study," Heart Rhythm, 8(5):752-759 (2011).
Provost et al., (2010) "Electromechanical Wave Imaging of Normal and Ischemic Hearts in Vivo," IEEE Trans. Med. Imaging 29(3):625-635.
Qin et al., "The Natural Frequency of Nonlinear Oscillation of Ultrasound Contrast Agents in Microvessels," Ultrasound in Med. & Biol., vol. 33, No. 7, pp. 1140-1148, 2007.
Ramanathan et al., "Activation and repolarization of the normal human heart under complete physiological conditions," Proceedings of the National Academy of Sciences 103(16):6309-6314, Apr. 18, 2006.
Ramanathan et al., (2004) "Noninvasive electrocardiographic imaging for cardiac electrophysiology and arrhythmia," Nat Med 10(4):422-428.
Revell et al., "Computer Vision Elastography: Speckle Adaptive Motion Estimation for Elastography Using Ultrasound Sequences." IEEE Transactions on Medical Imaging, vol. 24, No. 6, pp. 755-766 (2005).
Rice et al., "Approximate model of cooperative activation and crossbridge cycling in cardiac muscle using ordinary differential equations," Biophys. J 95:2368-2390, Sep. 2008.
Rogers et al., "Age-associated changes in regional aortic pulse wave velocity," J Am Coll Cardiol, vol. 38(4), pp. 1123-1129, 2001.
Roth, B.J., "Influence of a perfusing bath on the foot of the cardiac action potential," Circulation Research, vol. 86, E19-E22, 2000.
Samuel et al., "An ex vivo study of the correlation between acoustic emission and microvascular damage," Ultrasound Med. Biol., vol. 35, No. 9, pp. 1574-1586, 2009.
Sandrin et al., "Time-resolved pulsed elastography with ultrafast ultrasonic imaging," Ultrason Imaging, vol. 21(4), pp. 259-272, 1999.
Sarvazyan et al., "Shear wave elasticity imaging: A new ultrasonic technology of medical diagnostics," Ultrasound Med Biol, vol. 24(9), pp. 1419-1435, Nov. 1998.
Scher et al., (1956) "The pathway of ventricular depolarization in the dog," Circ Res 4:461-469.
Sengupta et al.,(2008) "Electromechanical activation sequence in normal heart," Heart Fail Clin 4:303-14.
Shehata et al., (2009) "Myocardial tissue tagging with cardiovascular magnetic resonance," Journal of Cardiovascular Magnetic Resonance 11:55.
Shiina et al., "Real time tissue elasticity imaging using the combined autocorrelation method," J. Med. Ultrasonics, 29(autumn):119-128 (2002).
Sinkus et al., "High-resolution tensor MR elastography for breast tumour detection," Phys Med Biol, 2000, 45(6):1649-1664.
Spach et al., "Extracellular discontinuities in cardia muscle—Evidence for capillary effects on the action potential foot," Circulation Research, vol. 83, pp. 1144-1164, 1998.
Stewart et al., "Blood-eye barriers in the rat: Correlation of ultrastructure with function," J. Comp. Neurol., vol. 340, No. 4, pp. 566-576, 1994.
Sutherland, G.R., "Color Doppler Myocardial Imaging—Potential Applications in Acquired and Congenital Heart Disease," Acta Paediatr Suppl. 410: pp. 40-48, Aug. 1995.

(56) References Cited

OTHER PUBLICATIONS

Tanter et al., "Ultrafast compound imaging for 2-D motion vector estimation: application to transient elastography," IEEE Trans Ultrason Ferroelectr Freq Control, vol. 49(10), pp. 1363-1374, 2002.
Techavipoo et al., "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Techavipoo et al., "Temperature Dependence of Ultrasonic Propagation Speed and Attentuation in Excised Canine Liver Tissue Measured Using Transmitted and Reflected Pulses," The Journal of Acoustical Society of America, 115(6):2859-2865 (2004).
Vappou et al., "Quantitive Viscoelastic Parameters Measured by Harmonic Motion Imaging," Phys. Med. Biol., vol. 54, pp. 3579-3595, Mar. 2009.
"Vial" entry from Wikipedia [online] [retrieved on May 20, 2014]. Retrieved from the Internet <URL: http://en.wikipedia.org/wiki/Vial>.
Walker et al., "A Fundamental Limit on Delay Estimation Using Partially Correlated Speckle Signals," IEEE T Ultrason Ferr, vol. 42(2), pp. 301-308, Mar. 1995.
Walker et al., (1994) "A fundamental limit on the performance of correlation based phase correction and flow estimation techniques," Ultrasonics, Ferroelectrics and Frequency Control, IEEE Transactions on 41(5):644-654, Sep. 1994.
Wang et al., "A composite high frame-rate system for clinical cardiovascular imaging," IEEE Transactions on Ultrasonics, Ferroelectrics, and Frequency Control, vol. 55(10), pp. 2221-2233, Oct. 2008.
Wang et al., "A composite imaging technique for high frame-rate and full-view cardiovascular ultrasound and elasticity imaging," IEEE International Ultrasonics Symposium, New York, NY, Oct. 28-31, 2007.
Wang et al., "Increased aortic stiffness assessed by pulse wave velocity in apolipoprotein E-deficient mice," Am J Physiol Heart Circ Physiol, vol. 278, No. 2, pp. H428-H434, 2000.
Wyman et al., (1999) "Mapping propagation of mechanical activation in the paced heart with MRI tagging," Am J Physiol Heart Circ Physiol 276:H881-891.
Yuh et. al., "Delivery of Systemic Chemotherapeutic Agent to Tumors by Using Focused Ultrasound: Study in a Murine Model," Radiology, 234(2): 431-437, 2005.
Zerhouni et al., "Human Heart: Tagging with MR imaging—a method for noninvasive assessment of myocardial motion," Radiology 169(1): 59-63, Oct. 1988.
Zheng et al., "Ultrasonic measurement of depth-dependent transient behaviors of articular cartilage under compression," *Journal of Biomechanics*, 38:1830-1837 (2005).
Zheng et al., "High Resolution ultrasound elastomicroscopy imaging of soft tissues: system development and feasibility," *Physics in Medicine and Biology*, vol. 49, No. 17, pp. 3925-3938 (Sep. 7, 2004).
Zwanenburg et al., (2004) "Timing of cardiac contraction in humans mapped by high-temporal-resolution MRI tagging: early onset and late peak of shortening in lateral wall," Am J Physiol Heart Circ Physiol 286: H1872-1880.
Branson Sonifier Cell Disrupter—Continuous Flow Attachment. Datasheet [online]. Branson Ultrasonics Corporation, 1998 [retrieved on Aug. 10, 2010]. Retrieved from the Internet: <URL: http://www.sonifier.com/pdf/CONTINUO.pdf>.
Wyslouzil, H.E., "Mineral Producers Improve Plant Performance Using Column Flotation Technology," [online], [retrieved on Feb. 23, 2010]. Retrieved from the Internet <URL: http://en-ca.eriez.com/Products/columncell0/Documents/benefitsofcolumnflotation/>.
Wyslouzil, H.E., "The Use of col. Flotation for the Recovery of Ultra-fine Phosphates," [online], [retrieved on Feb. 23, 2010]. Retrieved from the Internet <URL: http://en-ca.eriez.com/Products/columncell0/Documents/flotationofultrafinephosphates/>.

Szoka et al., "Comparative properties and methods of preparation of lipid vesicles (liposomes)," Annual Review of Biophysics and Bioengineering, Jun. 1980, vol. 9(1), pp. 467-508.
Taylor et al., "Targeted retroviral gene delivery using ultrasound," The Journal of Gene Medicine, Feb. 2007, vol. 9(2), pp. 77-87.
Thomson et al., "Manufacture of concentrated, lipid-based oxygen microbubble emulsions by high shear homogenization and serial concentration," Journal of Visualized Experiments: JoVE, Issue 87, May 26, 2014, pp. 1-7.
Tsutsui et al., "The use of microbubbles to target drug delivery," Cardiovascular Ultrasound, Dec. 2004, vol. 2 (1), pp. 23-29.
Unger et al., "Therapeutic applications of lipid-coated microbubbles," Advanced Drug Delivery Reviews, May 2004, vol. 56(9), pp. 1291-1314.
Vandenbroucke et al., "Ultrasound assisted siRNA delivery using PEG-siPlex loaded microbubbles," Journal of Controlled Release, Mar. 2008, vol. 126(3): pp. 265-273.
Wiencek et al., "Albumin spheres as contrast agents," In Advances in Echo Imaging Using Contrast Enhancement, Springer, Dordrecht, 1993 (full date is not available), pp. 57-70.
Written Opinion for International Application No. PCT/US2011/034704 dated Aug. 18, 2011.
Wyslouzil, "Mineral Producers Improve Plant Performance Using Column Flotation Technology," [online], [retrieved on Feb. 23, 2010]. Retrieved from the Internet.
Wyslouzil, "The use of column flotation for the recovery of ultra-fine phosphates," 2009 [online], [retrieved on Feb. 23, 2010]. Retrieved from the Internet.
Yao et al., "Ostwald ripening in two and three dimensions," Physical Review B, Apr. 1992, vol. 45(14), pp. 8173-8176.
Allcock et al., "An ionically cross-linkable polyphosphazene: poly[bis(carboxylatophenoxy)phosphazene] and its hydrogels and membranes," Macromolecules, Jan. 1989, vol. 22(1), pp. 75-79.
Allcock et al., "Glyceryl polyphosphazenes: synthesis, properties, and hydrolysis," Macromolecules, Jul. 1988, vol. 21(7), pp. 1980-1985.
Allcock et al., "Hydrolysis pathways for aminophosphazenes," Inorganic Chemistry, Feb. 1982, vol. 21(2), pp. 515-521.
Allcock et al., "Synthesis of sugar-substituted cyclic and polymeric phosphazenes and their oxidation, reduction, and acetylation reactions," Macromolecules, May 1983, vol. 16(5), pp. 715-719.
Bartlett, "Phosphorus assay in column chromatography," Journal of Biology and Chemistry, Mar. 1, 1959, vol. 234(3), pp. 466-468.
Bisazza et al., "Microbubble-mediated oxygen delivery to hypoxic tissues as a new therapeutic device," Proceedings of the Annual International Conference of the IEEE Engineering in Medicine and Biology Society, Aug. 20-24, 2008, pp. 2067-2070.
Boussif et al., "A versatile vector for gene and oligonucleotide transfer into cells in culture and in vivo: Polyethylenimine," Proceedings of the National Academy of Sciences of the United States of America, Aug. 1995, vol. 92(16), pp. 7297-7301.
Cavalieri et al., "Stable polymeric microballoons as multifunctional device for biomedical uses: synthesis and characterization," Langmuir, Sep. 13, 2005, vol. 21(19), pp. 8758-8764.
Chappell et al., "Targeted delivery of nanoparticles bearing fibroblast growth factor-2 by ultrasonic microbubble destruction for therapeutic arteriogenesis," Small, Oct. 2008, vol. 4(10), pp. 1769-1777.
Chen et al., "Architectural Acoustics and Noise: Advancements and Best Practices in Instrumentation for Architectural Acoustics and Noise," J. Acoust. Soc. Am.; 164th Meeting: Acoustical Society of America, 132(3, Pt. 2):1977-2018 (Sep. 2012).
Chen et al., "Engineering Acoustics and ASA Committee on Standards: Sound Intensity Measurements," J. Acoust. Soc. Am.; 164th Meeting: Acoustical Society of America, 132(3, Pt. 2):1984-1985 (Sep. 2012).
Chen et al., "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Cho et al., "Dynamic surface tension of stable air-filled microbubbles prepared by freeze-drying a solution of lipid/surfactant mixture," Colloids and Surfaces A: Physicochemical and Engineering Aspects, Aug. 2006, vol. 284, pp. 453-457.

(56) References Cited

OTHER PUBLICATIONS

Christiansen et al., "Targeted tissue transfection with ultrasound destruction of plasmid-bearing cationic microbubbles," Ultrasound in Medicine and Biology, Dec. 2003, vol. 29(12), pp. 1759-1767.
Cortesi et al., "Sugar cross-linked gelatin for controlled release: microspheres and disks," Biomaterials, Sep. 1998, vol. 19(18), pp. 1641-1649.
Epstein et al., "Preparation of alendronate liposomes for enhanced stability and bioactivity: in vitro and in vivo characterization," The AAPS Journal, Dec. 2008, vol. 10(4), pp. 505-515.
Epstein-Barash et al., "Prolonged duration local anesthesia with minimal toxicity," Proceedings of the National Academy of Sciences of the United States of America, Apr. 2009, vol. 106(17), pp. 7125-7130.
Feshitan et al., "Microbubble size isolation by differential centrifugation," Journal of Colloid and Interface Science, Jan. 15, 2009, vol. 329(2), pp. 316-324.
Fischer et al., "Effect of Poly(Ethylene Imine) molecular weight and pegylation on organ distribution and pharmacokinetics of polyplexes with oligodeoxynucleotides in mice," Drug Metabolism and Disposition, Sep. 2004, vol. 32(9), pp. 983-992.
Grolleman et al., "Studies on a bioerodible drug carrier system based on polyphosphazene Part I. Synthesis," Journal of Controlled Release, Jan. 1986, vol. 3(1-4), pp. 143-154.
Guibal et al., "Noninvasive contrast-enhanced US quantitative assessment of tumor microcirculation in a murine model: effect of discontinuing anti-VEGF therapy," Radiology, Feb. 2010, vol. 254(2), pp. 420-429.
Haag et al., "Microbubble-enhanced ultrasound to deliver an antisense oligodeoxynucleotide targeting the human androgen receptor into prostate tumours," The Journal of Steroid Biochemistry and Molecular Biology, Dec. 2006, vol. 102(1-5), pp. 103-113.
Hern et al., "Incorporation of adhesion peptides into nonadhesive hydrogels useful for tissue resurfacing," Journal of Biomedical Materials Research, Feb. 1998, vol. 39(2), pp. 266-276.
Huang, "Liposomes in ultrasonic drug and gene delivery," Advanced Drug Delivery Reviews, Jun. 2008, vol. 60(10), pp. 1167-1176.
International Preliminary Report on Patentability for PCT/US2011/034704 dated Nov. 6, 2012.
International Search Report and Written Opinion for International Application No. PCT/US2010/046854 dated Oct. 25, 2010.
Ito et al., "Dextran-based in situ cross-linked injectable hydrogels to prevent peritoneal adhesions," Biomaterials, Aug. 2007, vol. 28(23), pp. 3418-3426.
Ito et al., "The prevention of peritoneal adhesions by in situ cross-linking hydrogels of hyaluronic acid and cellulose derivatives," Biomaterials, Feb. 2007, vol. 28(6), pp. 975-983.
Kang et al., "A maelimide-based in-vitro model for ultrasound targeted imaging," Ultrasonics Sonochemistry, Jan. 2011, vol. 18(1), pp. 327-333.
Kheirolomoom et al., "Acoustically-active microbubbles conjugated to liposomes: Characterization of a proposed drug delivery vehicle," Journal of Controlled Release, Apr. 2007, vol. 118(3): pp. 275-284.
Kim et al., "Mechanical properties and microstructure of polycrystalline phospholipid monolayer shells: Novel solid microparticles," Langmuir, Sep. 30, 2003, vol. 19(20), pp. 8455-8466.
Klibanov, "Targeted delivery of gas-filled microspheres, contrast agents for ultrasound imaging," Advanced Drug Delivery Reviews, Apr. 5, 1999, vol. 37(1-3), pp. 139-157.
Korpanty et al., "Monitoring response to anticancer therapy by targeting microbubbles to tumor vasculature," Clinical Cancer Research, Jan. 2007, vol. 13(1), pp. 323-330.
Leong et al., "Bioerodible polyanhydrides as drug-carrier matrices. I: Characterization, degradation, and release characteristics," Journal of Biomedical Materials Research, Oct. 1985, vol. 9(8), pp. 941-955.
Leong et al., "Bioerodible polyanhydrides as drug-carrier matrices. II. Biocompatibility and chemical reactivity," Journal of Biomedical Materials Research, Jan. 1986, vol. 20(1), pp. 51-64.
Nair et al., "Novel Polymeric Scaffolds Using Protein Microbubbles as Porogen and Growth Factor Carriers," Tissue Engineering: Part C, 2010 (published online May 11, 2009), vol. 16(1), pp. 23-32.
Pitt et al., "Ultrasonic Drug Delivery—A General Review," Expert Opinion on Drug Delivery, Nov. 2004, vol. 1(1), pp. 37-56.
Ricardo et al., "Anginex-conjugated liposomes for targeting of angiogenic endothelial cells," Bioconjugate Chemistry, Mar. 2007, vol. 18(3), pp. 785-790.
Rooij et al., "Targeted ultrasound contrast agents for ultrasound molecular imaging and therapy," International Journal of Hyperthermia, Feb. 17, 2015, vol. 31(2), pp. 90-106.
Rosen et al., "Bioerodible polyanhydrides for controlled drug delivery," Biomaterials, Apr. 1983, vol. 4(2), pp. 131-133.
Rychak et al., "Deformable gas-filled microbubbles targeted to P-selectin," Journal of Controlled Release, Sep. 12, 2006, vol. 114(3), pp. 288-299.
Sapra et al., "Ligand-targeted liposomes for cancer treatment," Current Drug Delivery, Oct. 2005, vol. 2(4), pp. 369-381.
Schroeder et al., "Controlling liposomal drug release with low frequency ultrasound: mechanism and feasibility," Langmuir, Feb. 2007, vol. 23(7), pp. 4019-4025.
Schroeder et al., "Ultrasound, liposomes, and drug delivery: principles for using ultrasound to control the release of drugs from liposomes," Chemistry and Physics of Lipids, Nov. 2009, vol. 162(1-2), pp. 1-16.
Sirsi et al., "Effect of microbubble size on fundamental mode high frequency ultrasound imaging in mice," Ultrasound in Medicine & Biology, Jun. 2010, vol. 36(6), pp. 935-948.
Sirsi et al., "High-frequency ultrasound imaging of size-isolated microbubbles in mice," Proceedings of the IEEE International Ultrasonics Symposium, Sep. 2009, pp. 271-274.
Sirsi et al., "Microbubble compositions, properties and biomedical applications," Bubble Science Engineering and Technology, Nov. 2009, vol. 1(1-2), pp. 3-17.
Sirsi et al., "Polyplex-microbubble hybrids for ultrasound-guided plasmid DNA delivery to solid tumors," Journal of Controlled Release, Jan. 2012 (epublished Sep. 2011), vol. 157(2), pp. 224-234.
Streeter et al., "Improving sensitivity in ultrasound molecular imaging by tailoring contrast agent size distribution: in vivo studies," Molecular Imaging, Apr. 2010, vol. 9(2), pp. 87-95.
Swanson et al., "Phospholipid-stabilized microbubble foam for injectable oxygen delivery," Langmuir, Sep. 28, 2010, vol. 26(20), pp. 15726-15729.

* cited by examiner

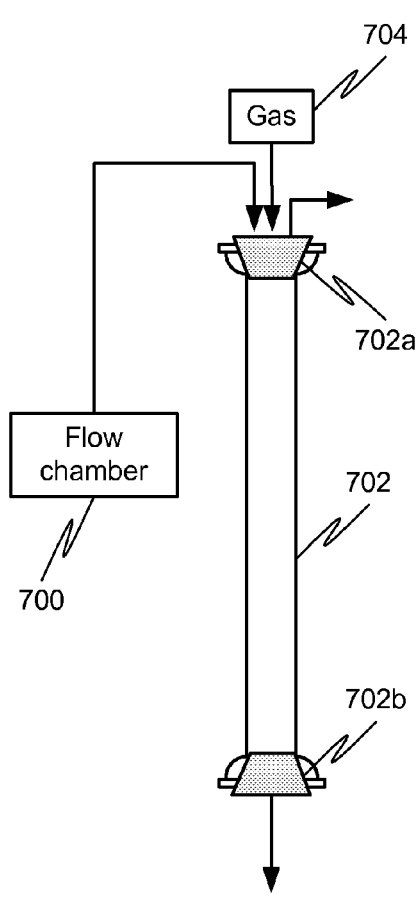
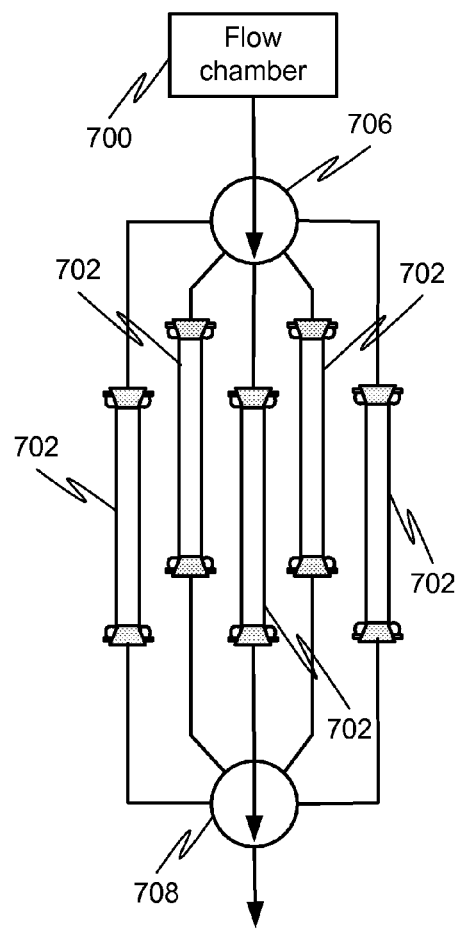
FIG. 7A
FIG. 7B
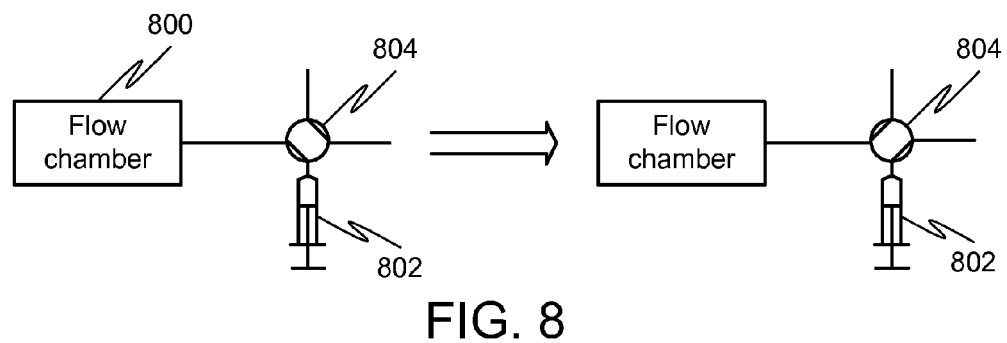
FIG. 8

SYSTEMS, METHODS, AND DEVICES FOR PRODUCTION OF GAS-FILLED MICROBUBBLES

CROSS-REFERENCE TO RELATED APPLICATIONS

The present application is a U.S. national stage of International Application No. PCT/US10/46854, filed Aug. 26, 2010, which claims the benefit of U.S. Provisional Application No. 61/237,892, filed Aug. 28, 2009, and U.S. Provisional Application No. 61/371,332, filed Aug. 6, 2010, all of which are hereby incorporated by reference herein in their entireties.

STATEMENT REGARDING FEDERALLY SPONSORED RESEARCH

The present invention was made with U.S. Government support under grant/contract no. 0952681 awarded by the National Science Foundation (NSF). The U.S. Government has certain rights in the invention.

FIELD

The present disclosure is directed to the generation of gas-filled bubbles, and, more particularly to systems, methods, and devices for production of gas-filled microbubbles for gas delivery.

BACKGROUND

Microbubbles have been used, for example, in the field of ultrasound imaging as contrast agents. However, such imaging applications require relatively few microbubbles, for example, on the order of $10^6$-$10^8$ microbubbles per injection. Such quantities can be achieved using low volume batch production techniques. However, for some medical and industrial applications, greater quantities of microbubbles may be required, for which low volume batch production techniques may be inadequate.

SUMMARY

A solution of gas-filled microbubbles can be synthesized using a flow chamber and a sonicator. The resulting microbubble solution can be size-sorted for a particular application, such as injection into a patient for gas delivery thereto. The microbubble solution may be concentrated to have greater than 50% volume gas while maintaining microbubble sizes below 10 μm. Control of the microbubble generation process can yield highly stable microbubbles. For example, the microbubbles may retain over half of their original gas payload for over three weeks while exhibiting minimal change in microbubble size. The systems, methods, and devices described herein can provide a continuous or batch-wise continuous supply of gas-filled microbubbles that readily release their gas payload when introduced into an under-saturated or de-saturated solution.

In embodiments, a microbubble generation system can include a sonicator member, a flow chamber, a level sensor, and a controller. The flow chamber can surround a portion of the sonicator member so as to define a reaction volume between an interior surface of the flow chamber and the surrounded portion of the sonicator member. The flow chamber can have a first inlet, a second inlet, and a first outlet. The flow chamber can be configured to permit a lipid solution to flow into the reaction volume through the first inlet and a gas to flow into the reaction volume through the second inlet. The flow chamber can also be configured to permit microbubbles generated in the reaction volume to be removed from the first outlet. An end of the sonicator member can be arranged so as to deliver ultrasonic energy to an interface between the lipid solution and the gas in the reaction volume. The level sensor can be configured to detect a level of the lipid solution in the flow chamber. The controller can be configured to control the lipid solution flow into the first inlet responsively to an output of the level sensor so as to maintain a location of said interface with respect to said end of the sonicator member such that the sonicator member is immersed in lipid solution to a level that is above an end of the sonicator member by no more than three times a gap between the end of the sonicator member and a wall of the flow chamber directly opposite the end of the sonicator member.

In embodiments, a method for generating microbubbles can include flowing a lipid solution at a first flow rate into a reaction volume of a continuous flow chamber, the reaction volume having an end of a sonicator member located therein. The method can further include flowing gas at a first pressure into the reaction volume at a same time as the flowing a lipid solution. An interface between the lipid solution and the gas in the reaction volume can be ultrasonically agitated using the sonicator member so as to generate a solution of gas-filled microbubbles. The method can also include, during the ultrasonically agitating, adjusting at least the first pressure based on a location of the interface in the reaction volume with respect to the end of the sonicator member. The method can further include ensuring the lipid solution ultrasonically agitated is saturated with a core gas to a level between 50% and 90%, inclusive, during the ultrasonically agitating.

In embodiments, another method of generating microbubbles can include, ultrasonically agitating a shell precursor in the presence of gas, and collapsing microbubbles a sufficient degree to strengthen the shells of the microbubbles. The collapsing can include regulating a saturation of the precursor to remain in a predefined range during the agitating.

Objects and advantages of embodiments of the present disclosure will become apparent from the following description when considered in conjunction with the accompanying drawings.

BRIEF DESCRIPTION OF THE DRAWINGS

Embodiments will hereinafter be described with reference to the accompanying drawings, wherein like reference numerals represent like elements. The accompanying drawings have not necessarily been drawn to scale. Where applicable, some features may not be illustrated to assist in the illustration and description of underlying features.

FIG. 7A is a schematic diagram of a setup using a microbubble separation column, according to one or more embodiments of the disclosed subject matter.

FIG. 7B is a schematic diagram of a setup using multiple microbubble separation columns, according to one or more embodiments of the disclosed subject matter.

FIG. 8 is a schematic diagram of a setup using a microbubble separation syringe, according to one or more embodiments of the disclosed subject matter.

DETAILED DESCRIPTION

Figure 1:
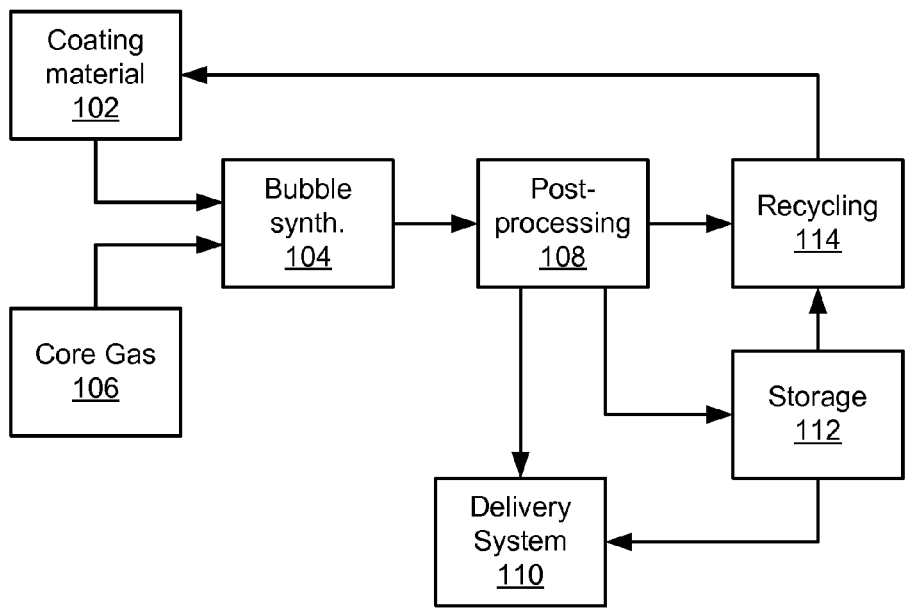
FIG. 1 is a schematic diagram of a microbubble generation system, according to one or more embodiments of the disclosed subject matter.

As used herein, microbubbles refer to roughly micron-sized (e.g., in the range of 1 μm to 10 μm in diameter) substantially-spherical gas-filled particles in solution that are stabilized by an organic coating at the gas-liquid interface. The stability, release of gas, and biocompatiblity of microbubbles can be controlled via the formulation of the coating material (i.e., the microbubble shell). Stability of the microbubbles can allow fabricated microbubbles to be stored for later use. Alternatively, the microbubbles may be used immediately after fabrication. In such cases, the coating material may be sufficiently stable so as to allow the microbubble to deliver its gas payload to an intended target (e.g., bloodstream of a patient).

Appropriate stability (e.g., on the order of days or weeks) of the microbubbles can be achieved using certain coating materials, as described herein. For example, mixtures of a phospholipid, such as dipalmitoylphosphatidylcholine (DPPC) or distearoylphosphatidylcholine (DSPC), and a polyethylene glycol (PEG) chain-based emulsifying agent (e.g., polyethylene glycol 40 stearate (PEG40S)) can be used for the microbubble coating. Such a coating self-assembles during the fabrication process thereby resulting in a microbubble coating layer of approximately 10 nm thick. The vast majority of the microbubble volume is thus available for gas storage. Such microbubbles can have a high surface area-to-volume ratio, which makes them ideal vehicles for the rapid delivery of gasses in a variety of applications. Moreover, the relatively small thickness of the coating presents a minor barrier to release of the gas. Because the materials for the microbubble coating are biologically derived, they also do not pose any biocompatibility concerns. The materials for the microbubble shell disclosed herein provide sufficient stability for use in biomedical applications and are relatively inexpensive; however, other materials may also be used to enhance microbubble stability.

The biocompatibility, gas delivery capability, and size of these microbubbles allow them to be used for gas delivery to a target, such as a patient. For example, by injecting the microbubbles filled with oxygen intravenously, the blood stream of a patient can be oxygenated in a minimally invasive manner. In embodiments, a microbubble generation system can produce large quantities of microbubbles, for example, a quantity sufficient to meet the respiratory needs of an average human (e.g., 200-250 mL of oxygen per minute). The concentration of the microbubble solution (i.e., the percent volume of gas in the solution) as well as the sizes of the microbubbles can be tailored for a specific application by appropriate control of the fabrication parameters of the microbubble generation system.

The microbubble generation system can provide a solution of microbubbles for use in a medical or other application. For example, the microbubble generation system can be configured to generate microbubbles on demand for immediate use. Alternatively, the microbubble generation system can be configured to provide a microbubble solution after a short startup delay (e.g., less than one minute). In another example, the microbubble generation system can be configured to continuously generate microbubbles without regard to demand. Any unused microbubbles may be discarded or recycled to generate more microbubbles. In still another example, the microbubble generation system can be configured to generate microbubbles in a batch-wise continuous process, whereby a batch of microbubbles is produced and stored onboard the system until such time it is needed by a user or process. The stored microbubbles would thus be immediately available for use and could be replaced or recycled at certain times to always maintain a fresh batch. Alternatively, the microbubbles may be stored external to the generation system. Of course, a commercial embodiment may incorporate one or more aspects of the above examples. For example, embodiments may operate in a normally batch-wise continuous mode with online storage but be able to supplement via continuous generation should demand exceed the amount stored.

In embodiments, the microbubble generation system can be a mobile system, such that the system can be moved, for example, from room to room in a hospital. In embodiments, the microbubble generation system can be deployed in mobile medical units, such an ambulance or medivac helicopter, for use by emergency personnel.

Alternatively, the microbubble generation system can be configured as a portable device that emergency responders can carry to a treatment site. In yet another alternative, the microbubble generation system can be a substantially fixed unit with appropriate fluid conveyances and/or storage vessels for transporting generated microbubbles to a target or treatment location.

In all embodiments, the lipid solution level may be controlled such that the sonicator member is barely immersed. In embodiments, the sonicator member may be immersed only such that the level of the lipid solution above the end of the sonicator member is no more than a gap between the wall of the reaction chamber opposite an end of the sonicator member. In embodiments, the level is controlled such that the sonicator member is immersed only such that the level of the lipid solution level lies above the end of the sonicator member substantially no more than three times the gap between the wall of the reaction chamber opposite an end of the sonicator member. In embodiments, the level is controlled such that the sonicator member is immersed only such that the level of the lipid solution level lies above the end of the sonicator member substantially no more than two times the gap between the wall of the reaction chamber opposite an end of the sonicator member. The gas flow and/or pressure, the lipid flow, or a combination of any of these may be used to regulate the lipid solution level in any of the embodiments.

FIG. 1 shows a microbubble generation system according to embodiments of the disclosed subject matter. A coating material 102, which is a microbubble shell precursor, various alternative embodiments of which are described elsewhere in the present specification, is supplied to a bubble synthesizing device 104 along with a gas 106 for the bubble core. The latter may be oxygen. The bubble synthesizing device 104 may be a sonication chamber as described elsewhere in the present specification. The bubble synthesizing device 104 creates microbubbles of a range of sizes in an atmosphere of pure core gas. The microbubbles can optionally be subjected to further processing in post-processing component 108. Post-processing component 108 can perform size selection and/or compaction, which results in microbubbles of a desired size range being isolated from fluid and microbubbles outside the desired range. Further, the compaction may include removal of a total gas volume that is consistent with high stability and maximum core gas by unit volume. In embodiments, the total gas volume delivered from the post processing component 108 is about 50%. The resulting material (i.e., cake) may be provided directly to a delivery system 110 for use, for example, a hypodermic needle for infusion. Alternatively, the cake can be provided to a storage system 112 where it is stored for later use.

Material that is rejected from the post-processing 108 may be recovered and processed in a recycling device 114 to replenish the supply of coating material 102. The recycling device 114 may also recover the gas from the unused material for reuse in core gas supply 106. The recycling device 114 may include a vacuum pump to draw a vacuum on material to remove any gas or bubbles from the solution. Alternatively or additionally, a bubble trap and/or bubble filter may used to remove bubbles from the solution to be recycled. Prior to removal of bubbles and gas, gas may be dissolved in the solution to saturate it as a step prior to removing. The recycling may also bring the saturation level of the coating material, at the temperature of bubble generation, to a target level, for example 50-90% saturation, by raising the temperature of the fluid to remove dissolved gas and then lowering the temperature to achieve the target saturation. Various pumps, fluid circuits, controllers, and other elements may be included in the device of FIG. 1 to provide the functionality described and with features as described elsewhere in the specification.

Figure 2:
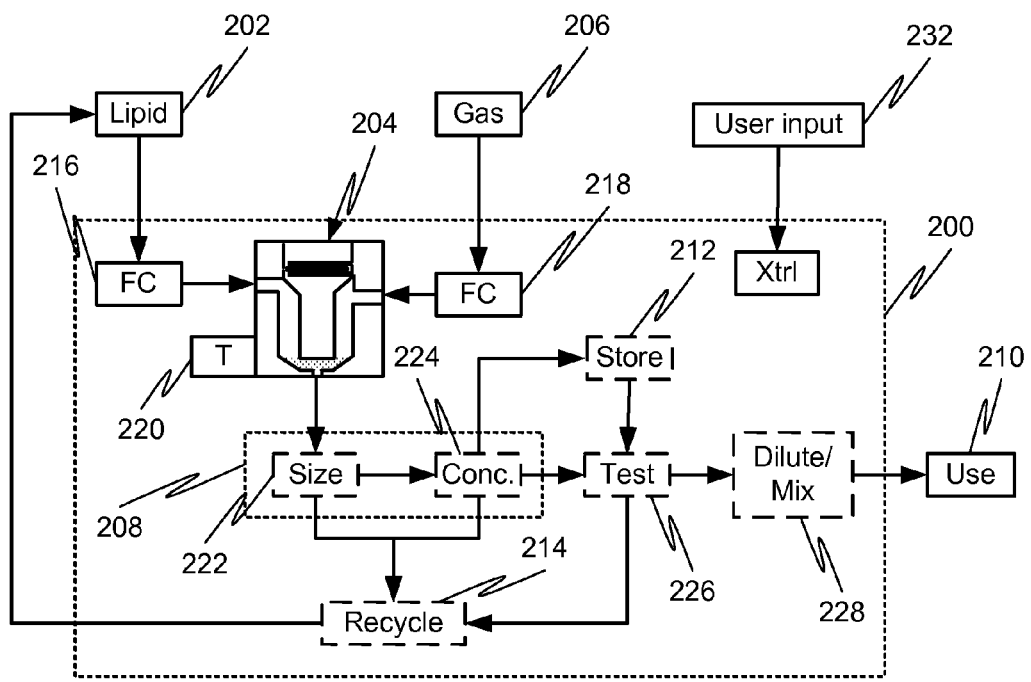
FIG. 2 is another schematic diagram of a microbubble generation system, according to one or more embodiments of the disclosed subject matter.

Referring to FIG. 2, a microbubble generation system 200 according to embodiments of the disclosed subject matter is shown. The microbubble generation system 200 can include a bubble synthesis module 204, which can have a sonicator in a flow chamber. The bubble synthesis module 204 can generate microbubbles from lipids conveyed from lipid supply 202 and a gas conveyed from gas supply 206. The bubbled system module 204 can consistently create large quantities of microbubbles having diameters of 10 μm or less in a continuous or batch-wise continuous manner. The microbubbles in this size range can be separated from other materials in the generated solution in size separation module 222, and then formed into a highly concentrated suspension (i.e., cake) in concentration module 224. Such a concentrated suspension can be stable during storage, such as onboard storage 212, but can also readily release the gas contained in the microbubbles upon introduction into a de-saturated or under-saturated solution.

A lipid solution from supply 202 can be introduced into the bubble synthesis module 204 via a flow control module 216. For example, flow control module 216 may be a pump controlled by a controller 230. The lipid solution may include a mixture of one or more phospholipids, for example, DPPC and/or DSPC. The lipid solution may also include one or more emulsifiers, for example, PEG. The lipid solution is delivered to the bubble synthesis module 204 at a controlled flow rate at the same time as gas via flow control module 218. For example, the gas flow control module 218 can include a valve, rotameter, and/or pressure regulator controlled by controller 230. The lipid solution and gas combine in the bubble synthesis module 204 where the application of ultrasonic energy results in microbubble formation. The temperature within the bubble synthesis module 204 during the ultrasonic application can be regulated by temperature regulation module 220, which may also be controlled by controller 230.

Microbubbles formed in the bubble synthesis module 204 can be conveyed to an optional post-processing module 208. Post-processing module 208 can include a size separation module 22 and a concentration module 224. The size separation module 222 can separate the microbubbles according to size so as to isolate the microbubbles having a diameter less than 10 μm for further use. For example, the isolated microbubbles can have diameters within a range of 1 μm to 10 μm, such as 2 μm to 5 μm. In embodiments, the size separation module 222 can operate on the principle of differential flotation, whereby larger bubbles will rise to the top of a solution in a gravity or other force field faster than smaller bubbles.

The initially isolated microbubble solution may be relatively dilute, for example, with a concentration of 1% volume gas. For certain applications, it may be desirable to increase the microbubble concentration so as to reduce the volume of fluid necessary to deliver a desired gas payload. The isolated microbubble may thus be concentrated in concentration module 224. The concentration module 224 may increase the concentration to greater than 50% volume gas for use and/or storage purposes using centrifugation or other methods as described elsewhere herein. Aspects of the size separation module 222 and concentration module 224 may be integrated together, for example, in a module that can provide both size separation and concentration, sequentially or simultaneously. Material discarded by the size separation module 222 and/or concentration module 224, such as excess lipids or solution, can be provided to recycling module 214 for processing and reuse in the production of additional microbubbles.

Microbubbles from optional post-processing module 208 may be available for immediate use 210, such as injection into a patient via an IV. Prior to being sent external to system 200 for use 210, the microbubble solution can be tested by test module 226. For example, test module 226 may inspect the microbubble solution for compliance with a desired microbubble size distribution, a desired gas concentration, and/or lipid material integrity. Size distribution may be measured using optical techniques, such as laser light obscuration and scattering. Gas concentration may also be determined using optical techniques, such as light obscuration. Lipid material integrity may be evaluated using chromatography or optical chromatography. In embodiments, the test module 226 may keep track of an expiration date or time of a particular solution or a particular batch of microbubbles (e.g., in storage 212). If the expiration date/time has been reached or if the solution did not pass one or more of the integrity tests, the test module 226 may direct the microbubble solution to recycling module 214 for reprocessing or disposal.

Alternatively, the microbubbles may be stored onboard in storage module 212 prior to use 210. Storage module 212 can include a temperature and/or pressure regulated container to contain the microbubble solution until ready for use. For example, storage module 212 can include a container or compartment internal to system 200 with an automatic pressure regulator to insure that the microbubbles are kept in a sealed environment filled with the core gas at atmospheric pressure. In embodiments, storage may be provided external to system 200, such as in a bottle, syringe, or other container. The external storage can have a pressure regulator, such as an automatic pressure regulator, to insure the microbubbles are kept in a sealed environment filled with the core gas at atmospheric pressure. The external storage can provide the microbubbles for use through a needle penetrating a septum of the container or via a needleless connector. Alternatively, the external storage can be a collapsed flexible container or bag. Microbubbles can be introduced into a bag in an evacuated/collapsed stage, thereby expanding the bag. Pressure regulation and/or gas purging of the flexible container may not be needed in such a configuration.

If the microbubble solution satisfies the testing by test module 226, the microbubbles can be conveyed to optional injection preparation module 228, which can prepare the microbubble solution for use 210. For example, where the microbubble solution is concentrated in cake form, the injection preparation module 228 may dilute the solution to a particular desired concentration and volume. In addition, injection preparation module 228 may include a mixer, which can mix the microbubble solution to provide homogeneity. Solution from preparation module 228 can then be delivered for use 210, for example, via a pump, such as but not limited to a syringe pump, a peristaltic pump, a diaphragm pump, or a shuttle pump.

Controller 230 is provided to control the various modules of the microbubble generation system 200, including but not limited to the bubble synthesis module 204, lipid flow control module 216, gas flow control module 218, temperature regulation module 220, post-processing module 208, test module 226, recycling module 214, and preparation module 228. Controller 230 may also control various fluid conveyances and/or valves within system 200. In addition, controller 230 can be configured to accept user input 232 and to control operation of system 200 based thereon. For example, user input 232 may include a desired microbubble size range. Controller 230 may regulate flow control modules 216 and 218, bubble synthesis module 204, and size separation module 22 to produce a microbubble solution with the desired size range. In another example, user input 232 may include a desired concentration and/or solution volume. Controller 230 may regulate the concentration module 224 and preparation module 228 to achieve the desired concentration and/or volume. Of course, the controller 230 may also control operation of system 200 based on other criteria as well, according to one or more contemplated embodiments.

System 200 may be embodied as a unitary device with lipid supply 202 and gas supply 206 provided separately. Alternatively, system 200, lipid supply 202, and gas supply 206 can be integrated together as a single device. In still another alternative, one or more components of system 200 may be integrated together while other components are separate. For example, lipid flow control module 216, gas flow control module 218, bubble synthesis module 204, and temperature regulation module 220 may be a single unit separate and distinct from post-processing module 208. In embodiments, certain components may be omitted from system 200 if unnecessary for a particular application. For example, post-processing module 208 may not be necessary for certain applications, such as industrial applications. In addition, one or more components of system 200 may be integrated with components of another processing system, such as an industrial processing system.

In embodiments, system 200 may include an onboard sterilization module (not shown) and/or operate in a substantially sterile environment, such that microbubbles produced would be available for immediate introduction into a patient. In embodiments, one or more components of system 200 may be disposable or replaceable with new sterile components. In an alternative, external sterilization modules, such as a UV sterilization unit, can be provided to sterilize the output of system 200 prior to use.

Figure 3:
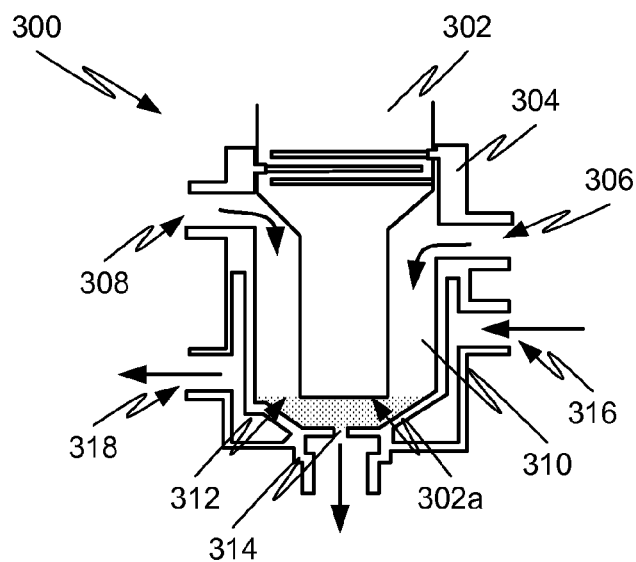
FIG. 3 is a schematic diagram of a sonicator and flow chamber setup, according to one or more embodiments of the disclosed subject matter.

FIG. 3 shows an example of a bubble synthesis module 300 that can be used in embodiments of a microbubble generation system. Synthesis module 300 can provide a substantially air-free environment for microbubble synthesis and collection. The flow chamber 304 of the module 300 has an ultrasonic horn 302 (i.e., sonicator) enclosed therein. A lipid solution injected into inlet 306 of the flow chamber 304 can be combined with a gas injected into inlet 308 of the flow chamber 304. The lipid solution can be delivered to the lower inlet 306 of the two side inlet ports 306, 308 of the flow chamber 304 by, for example, a pump (not shown).

The flow chamber 304 may have a reaction chamber 310 therein with a relatively high cup resulting in a shallow draft. Ultrasonic agitation (e.g., ~20 kHz) of the interface 312 between the lipid solution and the gas in the reaction volume 310 adjacent the tip 302a of horn 302 in the flow chamber 304 results in the production of gas-filled microbubbles. The generated microbubbles can be pulled from the shallow gap between the sonicator tip 302a and a bottom of the reaction chamber 310 via outlet 314, located at the bottom of the reaction chamber 310.

Figure 5:
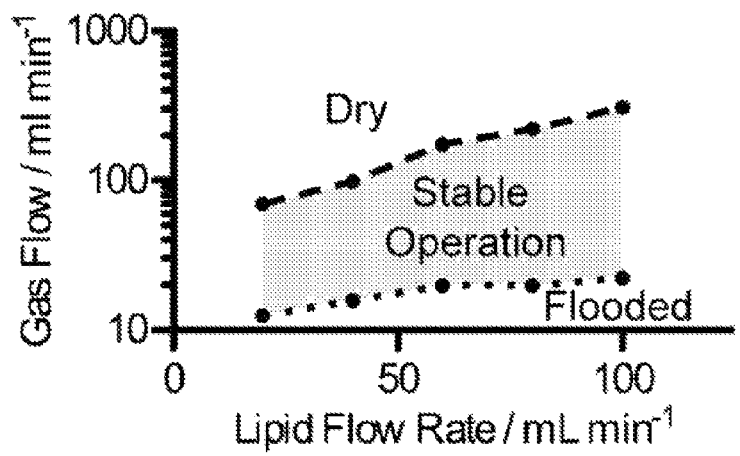
FIG. 5 is a graph illustrating flow chamber operation properties for various gas and lipid flow rates.

A cooling fluid, such as water, can be circulated through the flow chamber 304 via inlet port 316 and outlet port 318 to moderate the temperature of the reaction volume 310. For example, the cooling fluid can be circulated through an outer portion of the flow chamber 304 at 10° C. using a temperature control bath. The module 300 can handle lipid solution flow rates in excess of 100 ml/min with no detectable change in resulting microbubble properties for a wide range of lipid and gas flow rates, as shown in FIG. 5.

An appropriate lipid mixture for use in producing microbubbles can include 90 mol % of 1,2-dipalmitoyl-sn-glycero-3-phosphocholine (DPPC), 10 mol % of polyethylene glycol stearate (PEG-40S), and phosphate buffered saline (PBS) solution. The DPPC, a saturated sixteen carbon chain phospholipid, can provide for low surface tension at the gas-liquid interface and is a major component of pulmonary surfactant. The stearate end of the PEG can facilitates lipid dispersion and decreases microbubble coalescence. The buffered saline solution can be used to maintain a constant pH. In addition, the organic compounds of the monolayer mixture can be used for the purpose of its neutral effects when injected into the bloodstream of a patient.

The continuous flow attachment allows the constant exposure of lipid solution and gas to high intensity sonication (e.g., ~20 kHz and 400 W) in a reaction chamber, the volume of which can be controlled. The gap between the sonicator tip and the bottom of the reaction volume is directly related to the power density of the sonicator and thus can be optimized for efficient microbubble production. The sonicator probe 302 can be screwed into the flow chamber 304. The number of turns that the probe 302 is screwed into the flow chamber 304 can determine the volume of the reaction chamber gap.

The operating conditions of the sonicator 302 can be at its highest power intensity (e.g., 400 W), with a lipid flow rate of, for example, 108.7 ml/min, a gas flow rate of 75 ccm, and a $1/4$ gap turn in the flow chamber. These operating conditions can result in the formation of microbubbles less than 10 μm in size. The microbubble generation device serves to direct the gas, such as oxygen, and the lipid composition into the reaction volume, and specifically into a gap between the sonicator probe tip and the bottom outlet of the flow chamber. For example, oxygen flow can be initially set to approximately 60 mL/min. The lipid solution flow rate can be set to approximately 80 mL/min. When the lipid solution reaches the reactor, the sonicator can be turned on to a maximum power output.

In embodiments, operating the sonicator at a significantly high power density can be a factor that leads to concentrated bubbles of the size interest (~2 μm). By decreasing the gap to only a quarter turn so that the gap is on the order of, or less than, a millimeter, the lipid flow rate can increase without affecting the quality of the microbubbles. Flowing oxygen (when the core gas is oxygen) into the reaction chamber can keep the lipid mixture oxygenated and can level the lipid interface for a maximal oxygen entrainment process. When the lipid level rises above the sonicator probe end, bubbles may not be produced; rather, the sonicator may only further disperse the lipid mixture. Increasing the flow of oxygen can help stabilize any excessive flow rate of the lipid.

Figure 4:
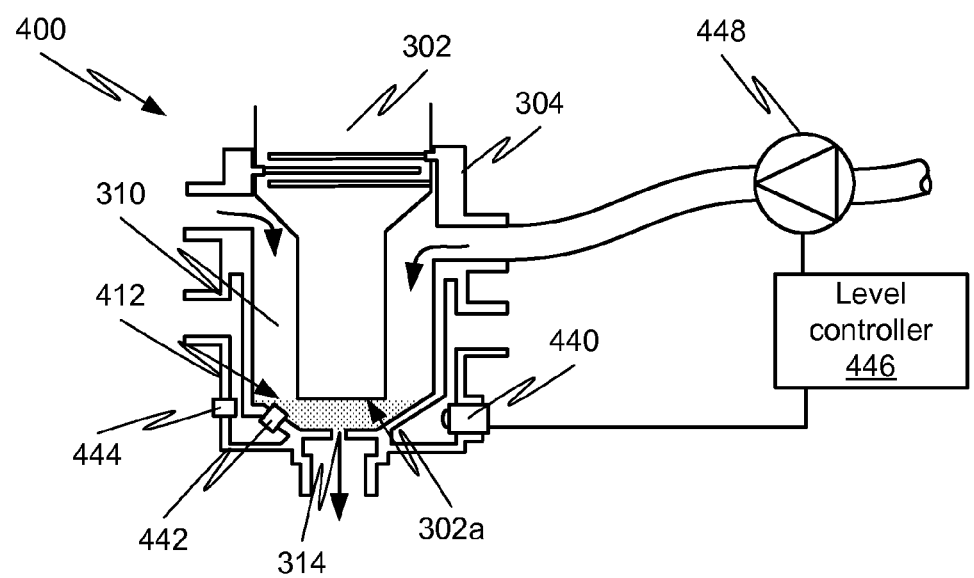
FIG. 4 is a schematic diagram of another sonicator and flow chamber setup with fluid level control, according to one or more embodiments of the disclosed subject matter.

Referring to FIG. 4, the bubble synthesis module of FIG. 3 can be modified to include level control of the gas-lipid interface with respect to the end of the sonicator probe. Level control may be important in embodiments to ensure that ultrasonic energy is not dissipated due to the actuator 302 being excessively immersed in microbubble shell precursor fluid. In embodiments, the fluid level is barely above the bottom 302a of the ultrasonic probe 302. To provide level control of interface 412, the rate of flow of precursor solution is feedback regulated by a controller 446 responsively to a detected level or other signal. For example, an optical detector 440 may be provided to indicate a proper or improper level. Alternatively, a pressure energy detector 442 (e.g., an ultrasonic microphone and energy transducer; for example, power spectral density function generator) may be used to generate a signature of the various on-level and off-level states of the sonicator system. Another example is a microphone 444 and recognition engine (incorporated in level controller 446 embodiments) which can indicate the operating state by an acoustical signature resulting from high, low, and correct-level operating states. The recognized operating state may be used to generate a feedback signal to the flow pump 448 to maintain a target level. In embodiments, an additional actuator (not shown) and control system may be provided to move sonicator probe 302 with respect to the flow chamber 304 so as to regulate the size of the gap between the end of the sonicator probe and the bottom of the reaction volume 310.

Figure 6:
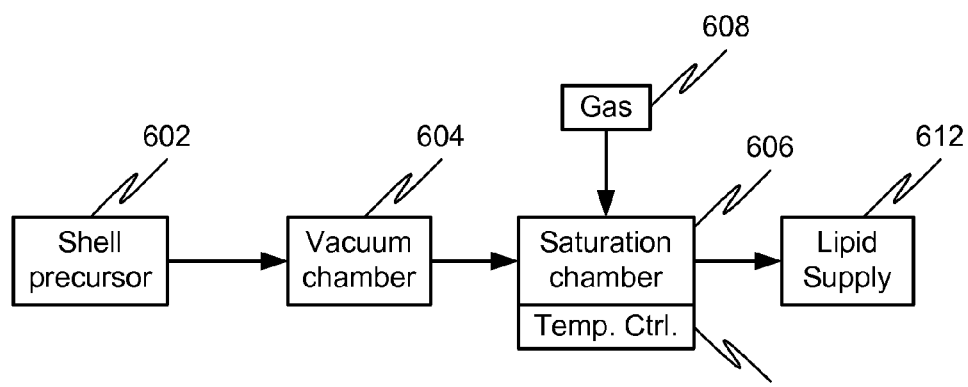
FIG. 6 is a schematic diagram of a lipid preparation module, according to one or more embodiments of the disclosed subject matter.

FIG. 6 illustrates conditioning of a shell precursor 602, such as a new solution of lipids and/or recycled lipid solution, prior to use as lipid supply 612 in microbubble generation. Any bubbles and/or trapped air/gas may be removed from the precursor solution such as by drawing a vacuum on the fluid in vacuum chamber 604 or passing through a bubble trap filter (now shown). Prior to removal of bubbles, however, gas may be dissolved in the solution to saturate it as a step prior to removing. For example, this could be done by injecting the intended gas with a sparger or by injecting microbubbles whose core gas is the same as the intended core gas. A saturation chamber 606 is a temperature controlled vessel (e.g., by temperature controller 610) that raises the temperature to a predefined level and then reduces the temperature to a level at which microbubbles are to be generated. Gas from source 608 can be introduced to the saturation chamber 606 to provide a substantially core gas environment therein. By raising the fluid temperature, dissolved gas evolves out of solution bringing the saturation to 100%. By then lowering the saturated gas to a target temperature, a predicted saturation level can be reached. A target level, for example 50-90% saturation may be achieved. In embodiments, the target saturation level is less than 100%. In other embodiments it is between 60 and 90%. Appropriate gas saturation levels for particular microbubble materials can be determined by experimentation. It has been found that a saturation level of less than 100% produces bubbles that have greater integrity than bubbles produced at a higher saturation. Some loss of gas within a newly formed bubble may densify the shell and create a more durable microbubble structure.

The setup of FIG. 6 may be applied to prepare a new solution of lipids for microbubble generation or to prepare a used solution for reuse, such as in recycling module 214 in FIG. 2. For an adequate dispersion of lipid aggregates, the lipid mixture can be heated in a water bath to a temperature above the main phase transition temperature (e.g., 41° C.) of DPPC. The lipid may then be saturated with oxygen. The bottles of lipid can be head-space exchanged, alternating multiple times between vacuuming and flowing oxygen over the solution.

In embodiments, the microbubbles formed by the bubble synthesis module can be separated from the foam and other large bubbles via flotation in a column 702, as shown in FIG. 7A. For example, the column 702 can be a 50 cm glass column. The column 7002 may be connected to the flow chamber 700 of the bubble synthesis module by an appropriate conduit. The mixture of microbubble solution and foam from the chamber 700 can flow into the top 702a of column 702. In embodiments, the solution may be introduced through the top of the column 702 but allowed to run down a sidewall thereof so as to reduce and/or prevent microbubble coalescence. The top 702a of the column 702 can be connected to a gas supply 704, used to purge the column after use as well as to create substantially core gas-filled interior volume prior to microbubble introduction. A vent in top 702a can ensure that the pressure in column remains substantially equal to atmospheric pressure.

After the column is filled with a microbubble-foam mixture, microbubbles in the column 702 are allowed to settle for a given period of time, during which larger bubbles rise into the foam layer while smaller bubbles remain closer to the bottom 702b. For example, 20-30 minutes can be given for the large bubbles to rise into the foam layer. Various fraction of the microbubbles can be extracted from the column via an outlet in bottom 702b of the column 702. The different fractions can have different size populations of microbubbles according to the settling time and the volume and location of the fractions within the column. In embodiments, a microbubble size population having diameters less than 10 μm (e.g., having diameters between 2 μm and 5 μm) can be selected by removing a particular fraction through the outlet at the column bottom 702b.

Because sufficient separation via flotation my take on the order of minutes, multiple columns 702 may be used to sort the microbubbles, as shown in FIG. 7B. A multiway valve 706 can be used to direct solution from flow chamber 700 to fill one of the columns as microbubbles in another column are allowed to settle. Valve 706 can switch to a different column 702 as each becomes full. Valve 708 can select between respective outlets of the different flow chamber 700 when sufficient settling has occurred for extraction of the desired microbubble size population.

Separation via differential flotation can be extended to different containers and/or arrangements. For example, a syringe 802 can be used to separate larger bubbles and foam from smaller microbubbles, as shown in FIG. 8. Microbubbles from flow chamber 800 can be directed into syringe 802 via valve 804. Once the syringe 802 is filled with the solution, the valve 804 can be switched. The fluid in the syringe can be allowed to settle, whereby larger bubbles and foam rise to the top while smaller bubbles remain closer to the bottom. The larger bubbles and foam can be dispense from the syringe by depressing the syringe plunger an appropriate amount, thereby leaving the smaller microbubbles in the syringe 802. The smaller microbubbles from the syringe 802 can be dispense at a later time through valve 804 or by connecting the syringe 802 to another fluid conveyance.

Figure 9A:
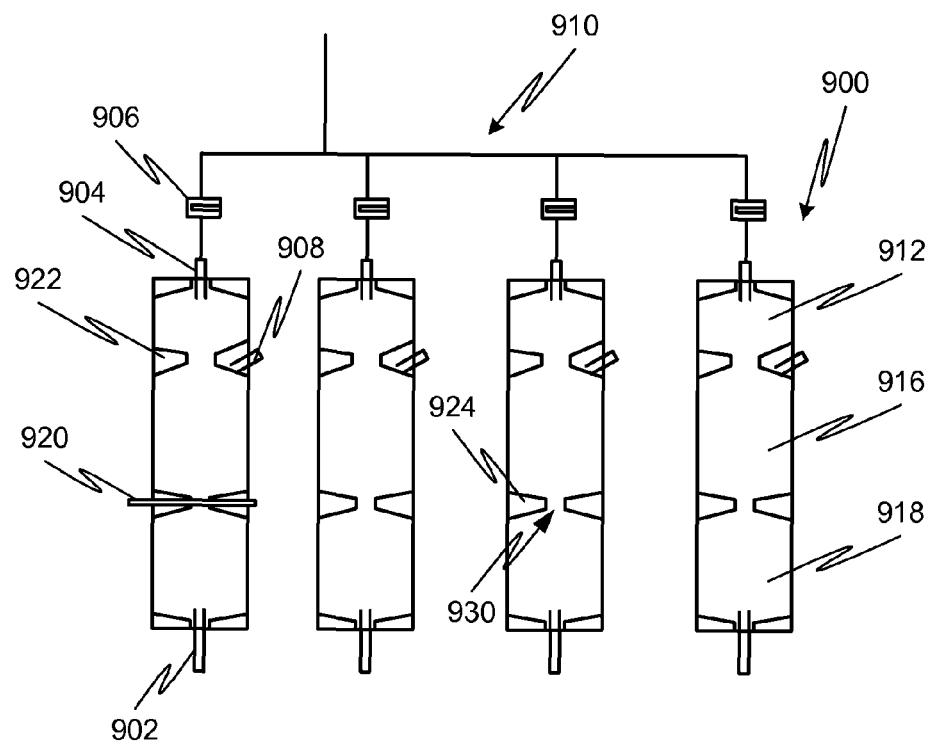
FIG. 9A is a schematic diagram of a setup using multiple flexible microbubble separation bags, according to one or more embodiments of the disclosed subject matter.

In embodiments, multiple flotation columns can be used in succession, as shown in FIG. 9A, in combination with the other elements of embodiments described elsewhere in the specification. The columns can be hermetically sealed bag containers 900 that are prefilled with a minimum quantity of gas, such as oxygen, such that the bag is collapsed and can be filled without venting. The bag containers 900 can be made of a gas impermeable laminate, for example. Alternatively, the bags may be purged with the core gas to initialize for use as described in the embodiments. In embodiments, the bags 900 may include multiple connectors and seal portions to allow parts of the bag to be isolated and to allow material to be selectively extracted and/or recycled from the bag.

For example, in the embodiment of FIG. 9A, a laminated bag 900 has multiple compartments 912, 916, 918 separated by clamping portions 922, 924. Each compartment can have a sealed connector 908. The clamping portions 922, 924 can be clamped by a clamp 920 device, which may be an automatic clamp forming part of a processor controlled device or a manual clamp, such that conduit 930 between adjacent compartments is effectively sealed off. Each chamber can have a respective outlet port 902 for removing cake product and/or precursor fluid, and a respective inlet port 904 for filling bag 900 from distribution line 910. A clamp 906 may isolate the bag 900 from the distribution line 910 once filled. For example, clamp 906 may be a non-reopenable clamp.

The bag can be delivered prefilled with oxygen and filled with the lipid solution directly from the sonicator. Then the bag can be held in a vertical orientation for a period of time to allow separation of small microbubbles from the larger bubbles and foam. After separation, the compartments may be clamped such a particular microbubble size population is isolated in one of the compartments. Microbubble solution can be drawn from the bag through, for example, port 908 and provided to a concentrating process, or the bag and its contents can be subjected to a concentrating process after a settling time. Alternatively, the bubbles in each compartment may be further allowed to settle thereby resulting in natural concentration of the bubbles therein near the top of the compartment.

Figure 9B:
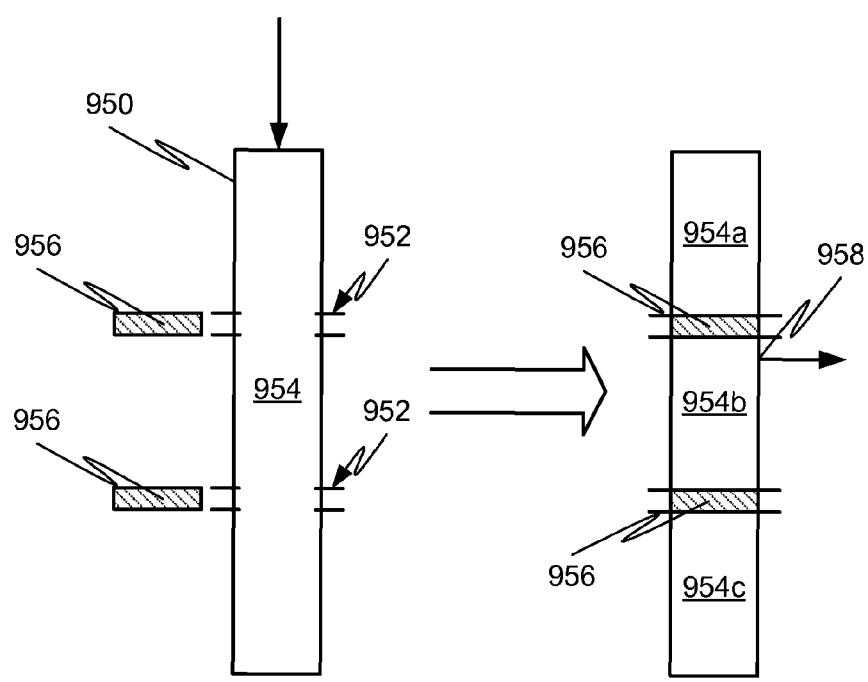
FIG. 9B is a schematic diagram of a setup using a partitioned microbubble separation container, according to one or more embodiments of the disclosed subject matter.

Any kind of suitable multi-compartment vessel may be used with embodiments. For example, the multi-compartment bag can be replaced by a rigid vessel such as a syringe structure to avoid the venting requirement or it can be a rigid vessel with a vent. Such a rigid structure 950 is shown in FIG. 9B. Microbubble solution may be injected into the interior volume 954. After a settling time, partitions 956 may introduced at locations 952 to form compartments 954a-c filled with isolated microbubbles. A port 956 can be used to withdraw the isolated microbubbles from a particular compartment (e.g., 954b).

Various alternative types of compartment containers may be provided and used in various ways as described. For example, a three compartment container can be filled with bubble solution and permitted to settle. After settling, a lower or middle portion of the container which is predicted (based on experiment or otherwise) to contain bubbles of suitable size is isolated by clamping a portion of the container separating the compartments. This portion may have two compartments, an upper and a lower. The container can be placed on a centrifuge and after centrifugation to separate the cake, the upper and lower compartments can be isolated from each other. The upper compartment contains the cake which is drawn out of the upper compartment with a syringe pump, shuttle pump, or other suitable device. The remaining material from the other compartments is recycled. This may be done by piercing the bag and passing the contents through a sterile filter for recycling to the sonicator.

In another example, a two compartment container can be filled with bubble solution and permitted to settle. After settling, a lower or middle portion of the container which is predicted (based on experiment or otherwise) to contain bubbles of suitable size is isolated as in the three compartment container. The container is placed on a centrifuge and after cake is formed, the cake is drawn from the container from a port that is located at a point known to coincide with the location of the cake. The cake can be removed without disturbing or mixing the liquid at the bottom.

In another example, a container can be filled with solution from the sonicator. The container is permitted to settle causing microbubbles to stratify at a predefined location of the container. The container is centrifuged and cake is withdrawn from a predefined zone of the container. Alternatively, the single compartment container can be allowed to settle for longer periods without being disturbed and cake withdrawn from a portion of the container where cake is formed. Alternatively, the two or three compartment container can be allowed to settle for longer periods without being disturbed until cake forms. The container may be clamped to isolate the cake from compartments above and below the cake and the cake stored and withdrawn from the compartment (or compartment portion in the two compartment embodiment) where cake is formed. Alternatively, in any of the embodiments, the non-cake contents of compartments or portions can be recovered by extraction and the container used for storage of the cake.

Figure 10:
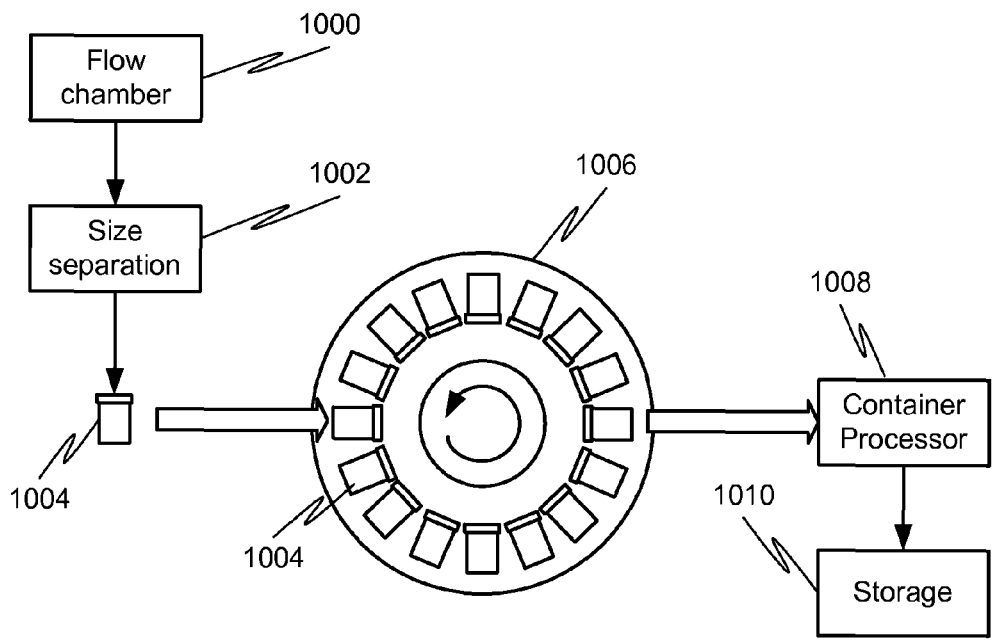
FIG. 10 is a schematic diagram of a setup using a centrifuge, according to one or more embodiments of the disclosed subject matter.

The microbubbles can be concentrated using centrifugation or another process that removes excess water and/or shell precursor material to place the microbubbles in cake form. Referring to FIG. 10, microbubbles directly from flow chamber 1000 or from size separation module 1002 can be loaded into containers 1004 for centrifugation in a centrifuge 1006. For example, the microbubbles can be centrifuged at 100 RCF (relative centrifugal force) for 5 minutes. In another example, the microbubbles can be centrifuged at 50 RCF for 15 minutes. The centrifuging may result in a separation within containers 1004 into a white viscous cake of microbubbles and an infranatant of lipid solution. After centrifuging, the infranatant in containers 1004 can be collected by container processing module 1008 and recycled or discarded. Syringes may be used for transfer without subjecting the microbubbles to destructive changes in pressure. Alternatively, suitable pumps, such as syringe pumps, shuttle pumps, diaphragm pumps, or other fluid conveyance devices may be used to handle the transfer of microbubbles through flow circuits within microbubble generation system 200. Centrifugation can be performed or repeated until the cake is approximately 50% or more gas by volume. The microbubble cake can be stored in syringes, for example, 12 mL syringes, capped with a three-way valve in a sealed glass jar or other suitable vessel as described in the instant specification. The microbubble cake can be stored in a substantially core gas atmosphere or in a container with zero excess volume, such as flexible bag.

Figure 11:
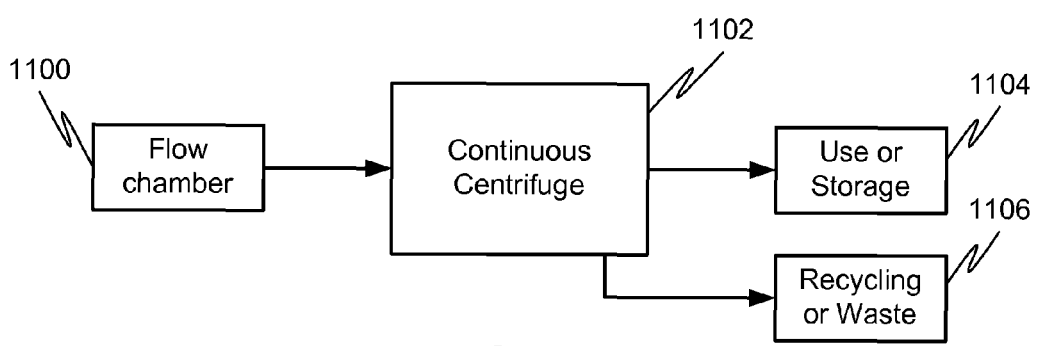
FIG. 11 is a schematic diagram of a setup using a continuous centrifuge, according to one or more embodiments of the disclosed subject matter.

In embodiments, aspects of concentration and size separation may be incorporated into a single device. For example, a continuous centrifuge 1102, as shown in FIG. 11, may be used to provide both size separation and concentration in a relatively continuous manner. Such a continuous centrifuge can be similar to that described in U.S. Pat. No. 4,842,738, entitled "Centrifuge Device," which is hereby incorporated by reference herein. In such embodiments, solution from flow chamber 110 is conveyed to continuous centrifuge 1102, which separates particles therein based on size. A concentrated size separated microbubble population can then be conveyed for use/storage 1104 while microbubbles having undesired sizes and excess solution are conveyed to recycling/waste 1106.

Figure 12:
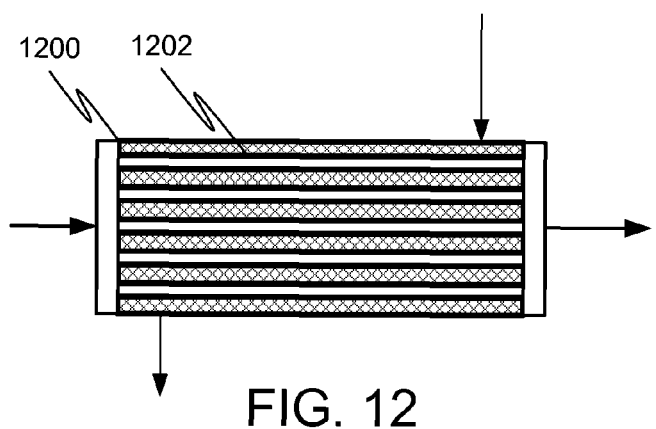
FIG. 12 is a schematic diagram of a dialyzer-based concentrator, according to one or more embodiments of the disclosed subject matter.

FIG. 12 shows a compaction device 1200 according to embodiments of the disclosed subject matter. A flow chamber 1202 has a membrane having a hyperosmolar solution on one side which dialytically extracts excess fluid from the microbubble fluid flowing on an opposite side of the membrane. This kind of device may provide an alternative or adjunct to centrifugation and permit continuous compaction of the microbubbles.

Figure 13:
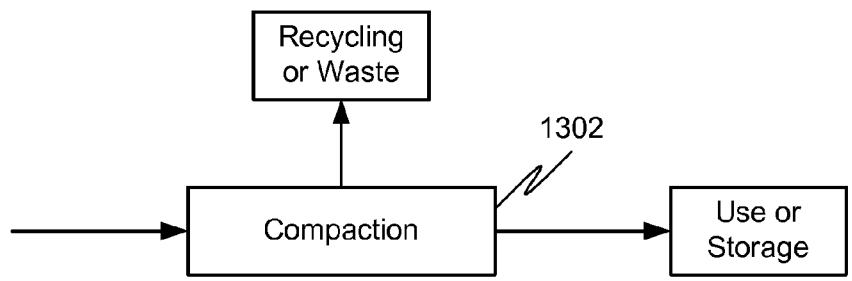
FIG. 13 is a schematic diagram of a setup using a compaction device, according to one or more embodiments of the disclosed subject matter.

FIG. 13 shows another compaction device 1300 according to embodiments of the disclosed subject matter. Microbubbles in solution are provided to flow chamber 1302, which may include an absorbent and/or dessicant therein. The absorbent and/or dessicant may be configured to remove excess fluid and/or lipids from the microbubble solution. This kind of device may provide an alternative or adjunct to centrifugation and permit continuous compaction of the microbubbles.

Figure 14:
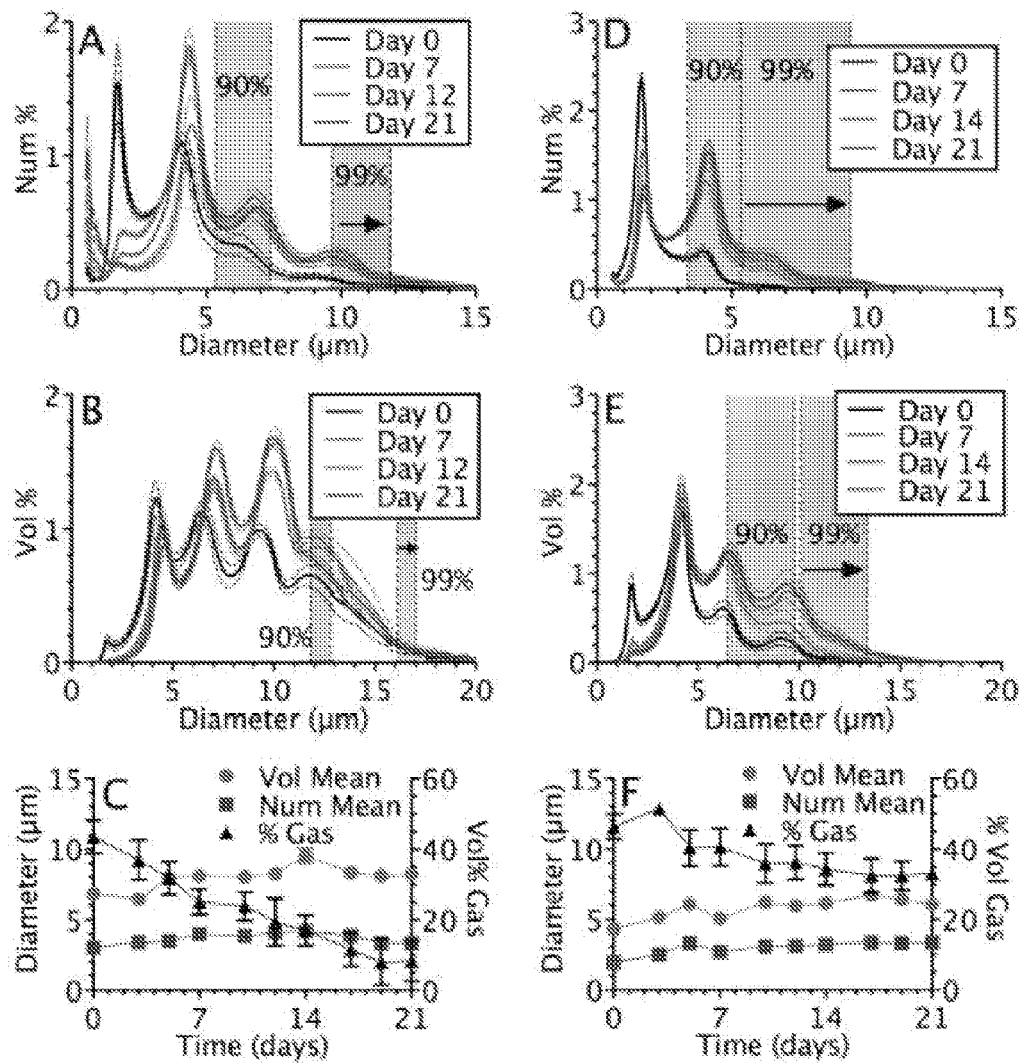
FIGS. 14A-14C show graphs of number percentage size distribution, volume weighted percentage size distribution, and mean diameters and percent volume gas over time of DPPC-based oxygen-filled microbubbles.
FIGS. 14D-14F show graphs of number percentage size distribution, volume weighted percentage size distribution, and mean diameters and percent volume gas over time of DSPC-based oxygen-filled microbubbles.

As discussed above, microbubbles produced using the disclosed microbubble generation system are relatively stable. Despite their different acyl chain lengths, the DPPC-based and DSPC-based coating formulations for the microbubbles yield similar initial properties, as shown in FIG. 14. FIGS. 14A and 14D represent the number percentage size distribution of DPPC-based oxygen-filled microbubbles and DSPC-based oxygen-filled microbubbles, respectively. FIGS. 14B and 14E represent the volume weighted percentage size distribution of DPPC-based oxygen-filled microbubbles and DSPC-based oxygen-filled microbubbles, respectively. FIGS. 14C and 14F represent the changes in mean diameters and percent volume gas over time of DPPC-based oxygen-filled microbubbles and DSPC-based oxygen-filled microbubbles, respectively. The size distributions of both formulations were polydisperse. Both yielded microbubbles with a series of preferred diameters, indicated by the peaks in the size distribution at 1-2 μm, 4-5 μm, 6-8 μm and 8-10 μm.

Most importantly from a biomedical point of view, the 99th percentiles (shown as grey vertical bars and labeled on FIGS. 14A-D, with arrows indicating change over time) show that all but 1% of the microbubbles are smaller than 12 μm for DPPC and 10 μm for DSPC. This can allow the microbubbles to clear the capillary beds of a patient and ensures minimal occlusion or embolism. The percentiles also change very little over time, indicating a level of stability sufficient for advance preparation and storage of microbubbles. While the particle size distributions of the highly concentrated microbubbles remain relatively constant over time, there was a slight shift during the first week, as illustrated in the number weighted and volume weighted mean diameters (FIGS. 14C and 14F). Aside from a slight initial increase, the mean microbubble diameter of DPPC-coated and DSPC-coated microbubbles does not change.

This stability could be due to a preferred polydispersity that requires time to achieve. While DPPC contains a shorter acyl chain (C16) and lower gel-to-liquid phase transition temperature (41° C. versus 55° C.), it also exhibits a smaller shift in both mean diameter and 99th percentiles over time. This apparent discrepancy could be explained by the higher initial polydispersity of DPPC-coated microbubbles, ostensibly starting closer to a more stable size distribution. This stable distribution could be related to the packing of microbubbles in the cake during storage, with a higher polydispersity leading to more point contacts between microbubbles and less deformation from their spherical shape.

Although the particle size distributions changed very little, percent volume gas of both formulations decreased linearly with time. The DPPC-coated microbubbles lose almost all of the gas enclosed in the microbubbles over the three-week testing period; however, DSPC-coated microbubbles retained gas within the microbubbles for a far longer period of time and still contained more than 30 vol % gas at the end of testing. Microbubble generation systems, as described herein, may thus detect this gas loss to determine when a particular batch of microbubbles, stored onboard or offline, has expired. Alternatively, the microbubble generation system may set an expiration date for stored microbubbles, for example, based on the particular microbubble shell material used, after which the microbubbles are discarded or recycled.

Figure 15:
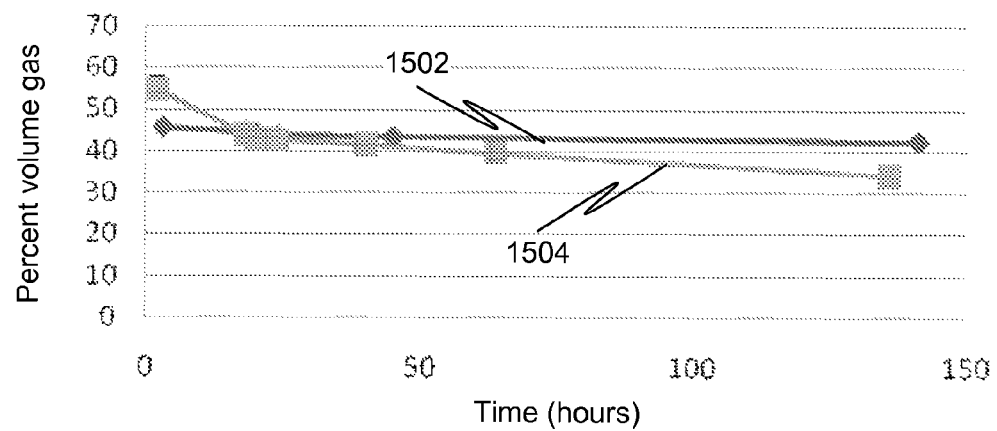
FIG. 15 is a graph comparing the percent volume gas in microbubbles in refrigerated and non-refrigerated storage conditions.

Storing microbubbles at lower temperatures can improve stability because, as the lipid shell becomes more solidified at cooler temperatures, gas, such as oxygen, should leave the microbubble at a slower rate. Since oxygen has a relatively high solubility, maintaining a system in a cooled setting may keep the lipid and microbubbles saturated in oxygen. Also, a cooler system would result in lower kinetic energy. A decreased movement of particles may result in a less chaotic and more controlled environment for the microbubbles. As shown in FIG. 15, by refrigeration of a microbubble cake, stability of the microbubbles can be improved. Over the course of six days, the refrigerated cake 1502 lost only about 5% of its oxygen; however, the non-refrigerated cake 1504 lost more than 15%.

Figure 16:
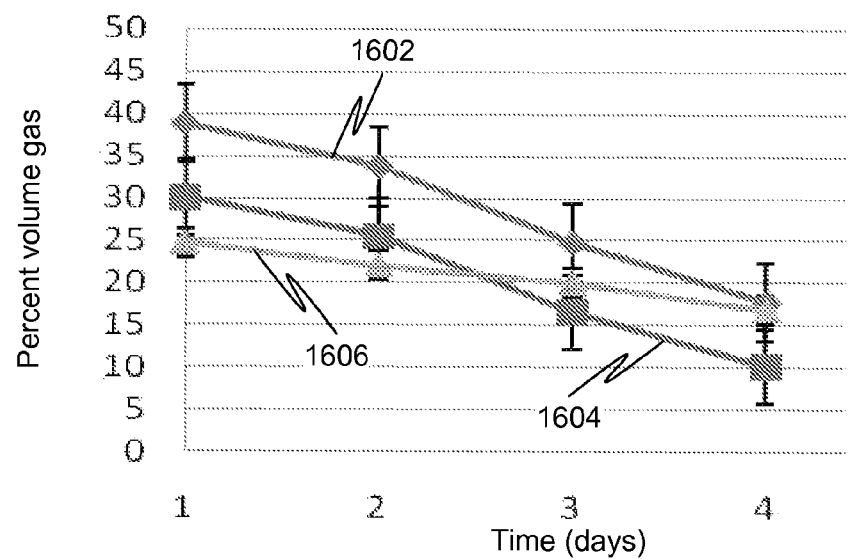
FIG. 16 is a graph comparing the percent volume gas in microbubbles at different cake densities with respect to time.
Figure 17A:
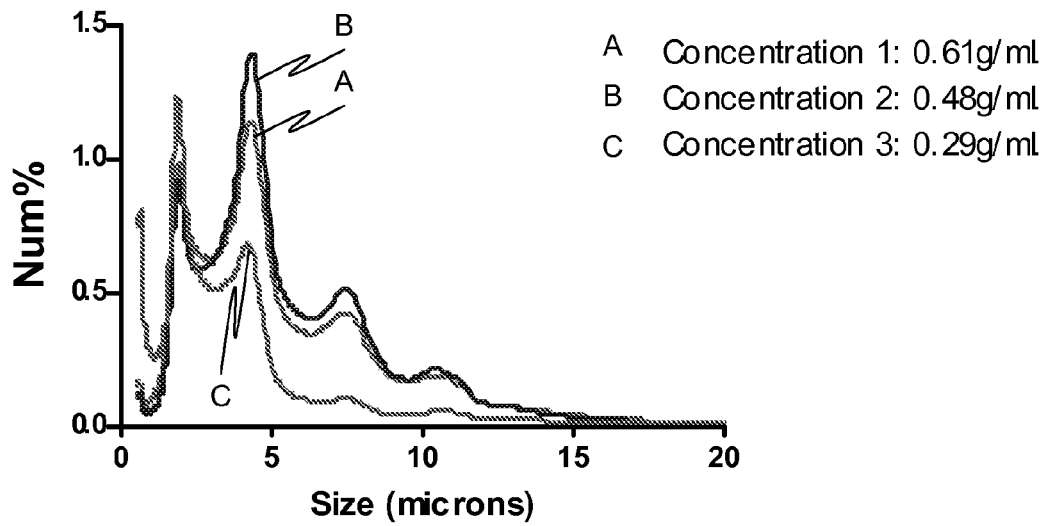
FIGS. 17A-17D are graphs showing the microbubble size distributions for different cake densities on different days.
Figure 17B:
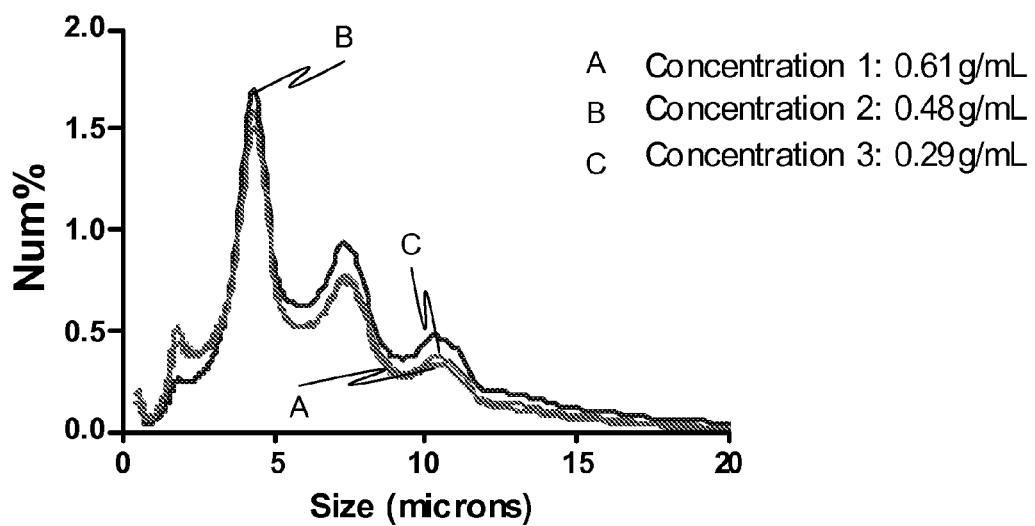
Figure 17C:
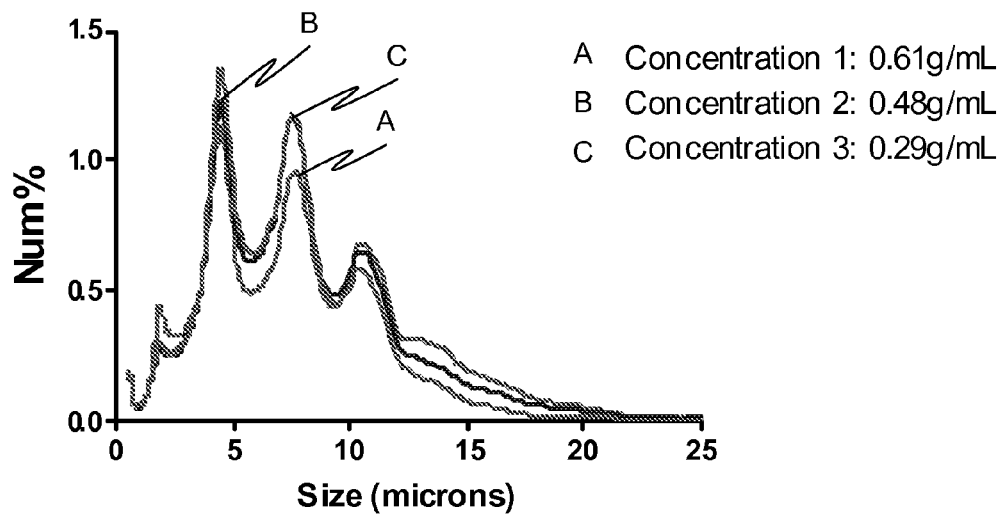
Figure 17D:
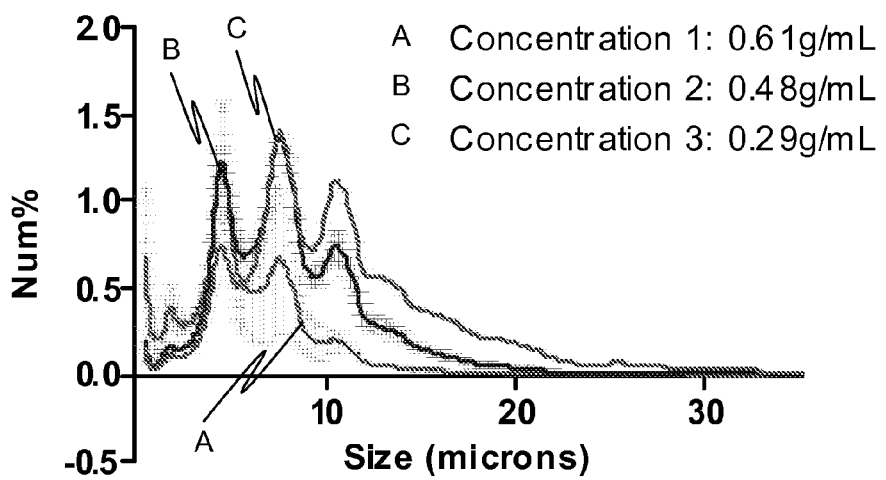

Keeping the microbubbles in a maximal core gas environment can aid in preventing rapid diffusion of the core gas through the lipid monolayer. For this reason, concentrating the microbubbles into a cake, in which gas-filled microbubbles were closely adjacent to other gas-filled microbubbles, may help reduce and/or minimize the diffusion of gas out of the respective cores. However, as shown in FIGS. 16-17, elevated concentrations may deter microbubble stability by encouraging coalescence of bubbles. Thus, keeping the bubbles in a slightly dilute sample may limit this occurrence.

Concentration stability testing was performed using three syringes, each with a different starting cake density (sample 1(1602): 0.61 g/mL, sample 2(1604): 0.48 g/mL, and sample 3(1606): 0.29 g/mL). Both size distributions and gas percentage (FIGS. 16-17) were measured over time. In day one, the size distributions of the samples vary; however, in the next two days the sizes become relatively uniform. By day four, the largest peak of sample 3 transitions from 2 to 8 µm. Sample 3 was the most dilute sample, yet it was able to maintain a relatively consistent oxygen percentage. While the bubbles of sample 3 are growing, there are fewer bubbles collapsing since oxygen is not rapidly leaving the solution. Sample 1 maintained the highest level of oxygen; however, it contained a sizable percentage of smaller bubbles (0-1 µm). The other two samples produced microbubbles of larger size ranges (5-8 µm), but gas percentages of less than that of sample 1. The oxygen percentage of sample 3 was observed to be more consistent. While samples 1 and 2 had the highest starting cake densities, the oxygen of those samples dissipated more quickly than that for sample 3. In addition, the gas percentage of sample 1 seems that it will reach values lower than those of sample 3.

When the gas encapsulated by the microbubble is oxygen, the resulting oxygen-containing microbubble solution may be used in a number of biomedical applications for, e.g., oxygen delivery to targeted organs or systems. Systemic delivery of metabolic oxygen to essential organs by the microbubbles could significantly improve the outcome of a variety of situations in critical care. Moreover, oxygen-containing microbubbles could improve tumor sensitization while simultaneously reducing immunogenic and renal side effects. Wound healing, organ preservation, and X-ray therapies are additional examples of biomedical applications that can be improved by application of a fluid containing a readily available source of oxygen, such as that available from microbubbles.

By injecting gas-filled microbubbles into a liquid, the gas can be readily dissolved therein and can equilibrate rapidly in the liquid flow stream (or in a particular liquid container or vessel). Such rapid gas-dissolution in a liquid can have numerous applications in industry and can enable novel techniques for handling of gas in solution. Industrial applications, such as, but not limited to, fermentation, remediation and other solution phase reactions of gaseous species could benefit from the high dissolution rates of microbubbles. In addition, the injection of microbubbles can take the place of or augment the use of a sparger in applications where such are used to dissolve gas. Examples include, but are not limited to, fuel cell applications. In such applications, size separation and/or concentration may not be necessary. In addition, different microbubble coating formulations, including formulations that may have improved stability as compared to the lipid formulations discussed herein, may be chosen which may be more compatible with a particular process.

Several microbubble populations may be prepared with different gas compositions contained therein. The resulting microbubble populations may then be introduced into the same solution, sequentially or simultaneously, to allow introduction and/or combination of the different gases in the solution. Different microbubble populations may also be injected into a solution at different times to, for example, ascertain the effect of different gases or to cause different effects in the solution or on a sample in solution. For example, where the solution contains a biological specimen, different gas compositions may be introduced at different times to cause different specimen behaviors or responses.

In addition, the microbubbles described herein may be useful in applications where introduction of gas into solution is traditionally difficult or impossible. For example, the microbubbles may be used to inject gas into fluid contained in a micro-channel or a nano-channel of a microfluidic or nanofluidic device. In another example, the microbubbles may be used to inject gas into fluid contained in a capillary or other tubing.

Moreover, microbubble injection points may be arranged so as to control the location of gas introduction into the solution. For example, where it is desired to introduce gas to a particular location, such as a target site or reaction site within the solution, the injection point may be located at or downstream from the particular location so as to deliver the gas payload thereto. In another example, injection points of different microbubble populations containing the same or different gases may be provided proximal to a target location so as to simultaneously or sequentially inject the gases at the target location. Of course, other applications for the gas-filled microbubbles described herein are also possible according to one or more contemplated embodiments.

Although particular configurations have been discussed herein, other configurations can also be employed. Furthermore, the foregoing descriptions apply, in some cases, to examples generated in a laboratory, but these examples can be extended to production techniques. For example, where quantities and techniques apply to the laboratory examples, they should not be understood as limiting. In addition, although the production of oxygen microbubbles has been specifically described herein, other gases (elemental or compositions) are also possible according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, systems, methods, and devices for producing gas-filled microbubbles. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A microbubble generation system comprising:
   a sonicator member;
   a flow chamber surrounding a portion of the sonicator member so as to define a reaction volume between an interior surface of the flow chamber and the surrounded portion of the sonicator member,
   the flow chamber having a first inlet, a second inlet, and a first outlet, configured to permit a lipid solution to flow into the reaction volume through the first inlet, and a gas to flow into the reaction volume through the second inlet, and further to permit microbubbles generated in the reaction volume to be removed from the first outlet,
   an end of the sonicator member being arranged so as to deliver ultrasonic energy to an interface between the lipid solution and the gas in the reaction volume; and
   a level sensor configured to detect a level of the lipid solution in the flow chamber;
   a controller configured to control the lipid solution flow into the first inlet responsively to an output of the level sensor so as to maintain a location of said interface with respect to said end of the sonicator member such that the sonicator member is immersed in lipid solution to a level that is above an end of the sonicator member by no more than three times a gap between the end of the sonicator member and a wall of the flow chamber directly opposite the end of the sonicator member.

2. The microbubble generation system of claim 1, further comprising a size separation module that sorts microbubbles removed from the reaction volume via the first outlet responsively to a size thereof,
   wherein the size separation module is configured to isolate microbubbles having a diameter less than 10 μm from the micro bubbles removed from the reaction volume, and
   the size separation module is configured to sort microbubbles using differential flotation.

3. The microbubble generation system of claim 2, wherein the size separation module includes a container with movable partitions arranged at different locations therein, the partitions being configured to form isolated compartments in the container.

4. The microbubble generation system of claim 1, further comprising a size separation module that sorts microbubbles removed from the reaction volume via the first outlet responsively to a size thereof,
   wherein the size separation module includes a flexible bag and a machine with a plurality of clamps arranged at different locations along the bag,
   the clamps being configured to clamp the flexible bag at their respective locations so as to form isolated compartments in the flexible bag,
   the isolated compartments include first and second compartments for isolating micro bubbles of different size ranges,
   the machine has a controller that is configured to first activate the clamps to isolate microbubbles of a predefined size range and subsequently isolate microbubbles that are compacted to predefined degree, and
   the machine is configured to centrifuge the flexible bag.

5. The microbubble generation system of claim 4, wherein the flexible bag includes at least one port, each port providing access to one of the isolated compartments in the flexible bag.

6. The microbubble generation system of claim 1, further comprising a concentration module configured to concentrate the microbubbles,
   wherein concentration module is configured to concentrate the microbubbles so as to have a concentration of at least 50% volume of gas, and
   the concentration module includes one of a centrifuge and a dialyzer.

7. The microbubble generation system of claim 1, wherein the first outlet is arranged at a lowest point of the reaction volume and opposite said end of the sonicator member in the reaction volume so as to define a gap therebetween.

* * * * *